(12) United States Patent
Lewis

(10) Patent No.: US 6,755,836 B1
(45) Date of Patent: Jun. 29, 2004

(54) BONE SCREW FASTENER AND APPARATUS FOR INSERTING AND REMOVING SAME

(75) Inventor: David H. Lewis, Fort Collins, CO (US)

(73) Assignee: High Plains Technology Group, LLC, Fort Collins, CO (US)

( * ) Notice: Subject to any disclaimer, the term of this patent is extended or adjusted under 35 U.S.C. 154(b) by 0 days.

(21) Appl. No.: 10/326,701

(22) Filed: Dec. 20, 2002

(51) Int. Cl.[7] .............................................. A61B 17/56
(52) U.S. Cl. .................................. 606/73; 606/104
(58) Field of Search ............................. 606/72, 73, 164

(56) References Cited

U.S. PATENT DOCUMENTS

| | | | | |
|---|---|---|---|---|
| 2,248,054 A | * | 7/1941 | Becker ........................ 81/457 |
| 2,329,398 A | * | 9/1943 | Duffy .......................... 606/104 |
| 3,604,487 A | * | 9/1971 | Gilbert ........................ 81/443 |
| 4,339,971 A | | 7/1982 | Zatorre ........................ 81/436 |
| 4,572,039 A | | 2/1986 | Desjardins ................... 81/451 |
| 5,312,438 A | * | 5/1994 | Johnson ....................... 606/232 |
| 5,353,667 A | | 10/1994 | Wilner ......................... 81/436 |
| 5,354,292 A | * | 10/1994 | Braeuer et al. ................ 606/1 |
| 5,484,440 A | * | 1/1996 | Allard ......................... 606/73 |
| D375,452 S | | 11/1996 | Housser ....................... D8/382 |
| 5,666,831 A | | 9/1997 | Doros ......................... 70/140 |
| 5,722,838 A | | 3/1998 | Czegledi ..................... 411/407 |
| 5,870,934 A | | 2/1999 | Cullinan ...................... 81/436 |
| 5,899,901 A | | 5/1999 | Middleton .................... 606/61 |
| 6,128,983 A | | 10/2000 | Arnn ........................... 81/460 |
| 6,183,479 B1 | * | 2/2001 | Tormala et al. ............. 606/104 |
| 6,234,914 B1 | | 5/2001 | Stacy .......................... 470/63 |
| 6,402,757 B1 | * | 6/2002 | Moore et al. ................. 606/80 |

* cited by examiner

Primary Examiner—Pedro Philogene
Assistant Examiner—David A Bonderer
(74) Attorney, Agent, or Firm—Santangelo Law Offices, P.C.

(57) ABSTRACT

A system for and methods of easily and securely inserting and removing a fastener usable during orthopedic surgery to promote proper healing of injured bone are disclosed. In at least one embodiment, the invention provides a system for positive, complete tri-modal retention of a bone media fastener element by a bone media fastener driver element so that three types of positional divergence of the driver relative to the fastener—bi-axial, bi-rotational, and bi-lateral—may be prevented. At least one embodiment of a bone media fastener apparatus may comprise a shaft element, a threaded bone engagement element, and a head element that itself may comprise a fastener-side, positive, complete tri-modal retention element that is engageable with a driver-side, positive, complete tri-modal retention element of a bone media fastener driver element to prevent bi-lateral divergence, bi-rotational divergence, and bi-axial divergence.

73 Claims, 16 Drawing Sheets

BONE SCREW FASTENER AND APPARATUS FOR INSERTING AND REMOVING SAME

BACKGROUND OF THE INVENTION

Generally, this invention relates to a system for and methods of easily and securely inserting and removing a fastener that in at least one application is used during orthopedic surgery to promote proper healing of injured bone. Specifically, the invention focuses upon a fastener and a corresponding driver that is usable to insert and remove the fastener in a manner that reduces the chance of slippage of the driver from the fastener—a problem in orthopedics, other branches of health care, and fastening generally.

Fasteners with threads, or screw fasteners, are commonly used to hold broken bones in place during healing and to attach orthopedic healing aids such as plates or rods to broken bones. In many healing applications, the fastener should have the ability to draw pieces of the bone into intimate contact, and/or the orthopedic healing aid into intimate contact with the bone(s) or bone pieces. The torque required to achieve this may be delivered by an insertion device or driver. Ideally, the fastening system will allow for quick insertion to minimize the time required for the procedure and will have sufficient engagement with the insertion device to prevent positional divergence such as slippage of the driver from the fastener which could cause the fastener to be improperly positioned and/or cause additional damage to the bone, among other problems. Additionally, the system will allow for secure non-slip insertion of the fastener without requiring an improperly high compressive force be imparted by a user to the driver. Finally, a removal device (which may be the same as the insertion device) must be able to securely reengage the fastener so it can be removed from the bone with a minimized chance of positional divergence of the driver from the fastener, also without requiring the application of an improperly high compressive force into the fastener to assure secure removal of the fastener.

Efforts in the driver/fastener system field have tended to focus on the design of thread systems to ensure intimate contact of bone fragments and/or of the orthopedic healing aid with bone(s). Examples of these efforts may be illustrated in U.S. Pat. Nos. 6,022,352, 6,083,227, and 5,871,486. While these technologies address an important problem, considerably less effort has been applied to the equally important problem of quickly, safely, and securely inserting and removing bone screw fasteners. Examples of efforts in this specific area are illustrated in U.S. Pat. Nos. 5,885,286; 6,048,343; 6,183,472; and 5,997,538. Several of these approaches are complex mechanical assemblies consisting of many small parts which may be difficult to assemble and manipulate, and that pose a hazard to the patient during orthopedic surgery. Often, the physician must take additional time to use these devices and ensure their proper assembly and disassembly. Thus, there is a need for a fastener/driver device that is not a complex mechanical assembly and that exhibits a positive, non-slip engagement between driver and fastener. Although this problem is well known on orthopedics and other fields of endeavor, the need for a simple system that facilitates the rapid, reliable and secure insertion and removal of fasteners has not been adequately met.

SUMMARY OF THE INVENTION

The present invention includes a variety of aspects and features which may be applied in various ways depending on the exact application or need to be addressed. At least one embodiment of his invention involves a system for the rapid and reliable insertion and removal of fasteners for use in orthopedic surgery and other applications requiring such capability. This system may include a fastener and a tool such as a driver that is usable for insertion and removal of the fastener. In one basic form, the invention provides a system for positive, complete tri-modal retention of a fastener by a fastener driver so that during operation of the system in a fully engaged configuration and under design loads, three types of positional divergence of the driver relative the fastener—bi-axial, bi-rotational, and bi-lateral—are prevented. Thus, relative to conventional fastener/driver systems, the fastener can be inserted and removed by the driver more quickly and with a reduced possibility of slippage, stripping, or other hazardous, undesired positional divergence of the driver from the fastener. The system is designed to better meet the needs of both the patient and the physician in orthopedic surgery and other areas of health care. It may also find use in other fastening applications such as structural assembly, whether in fields such as aerospace, aircraft or carpentry, as but a few examples.

An object of at least one embodiment of the invention is to provide an insertion/removal device such as a bone fastener driver that can be easily inserted into the head of a bone fastener, with a resultant positive, complete tri-modal retention of the driver to the fastener, where positive, complete tri-modal retention may include the prevention of each bi-lateral, bi-rotational, and bi-axial divergence of the driver from the fastener.

Another goal of at least one embodiment of the invention is to provide a positive retention driver/fastener system that is operable by a user who prefers to (or must) use only one hand.

A further feature of at least one embodiment of this invention may be to provide a positive retention element that may also facilitate proper alignment of the driver with the fastener.

Another goal of the invention is to enable the application of increased driving torques when necessary or desired without resulting in positional divergence of the driver from the fastener. Such increased torques may not have been possible with prior systems whose designs may have resulted in positional divergence (such as bi-axial, bi-lateral, or bi-rotational slippage) of the driver from the fastener during higher applied torque load operation, or whose designs may have required the application of an improperly high compressive axial force to assure secure driver-to-fastener engagement throughout the driving process.

BRIEF DESCRIPTION OF THE DRAWINGS

All drawings are intended merely as examples of at least one embodiment.

DETAILED DESCRIPTION OF THE PREFERRED EMBODIMENTS

Figure 1A:
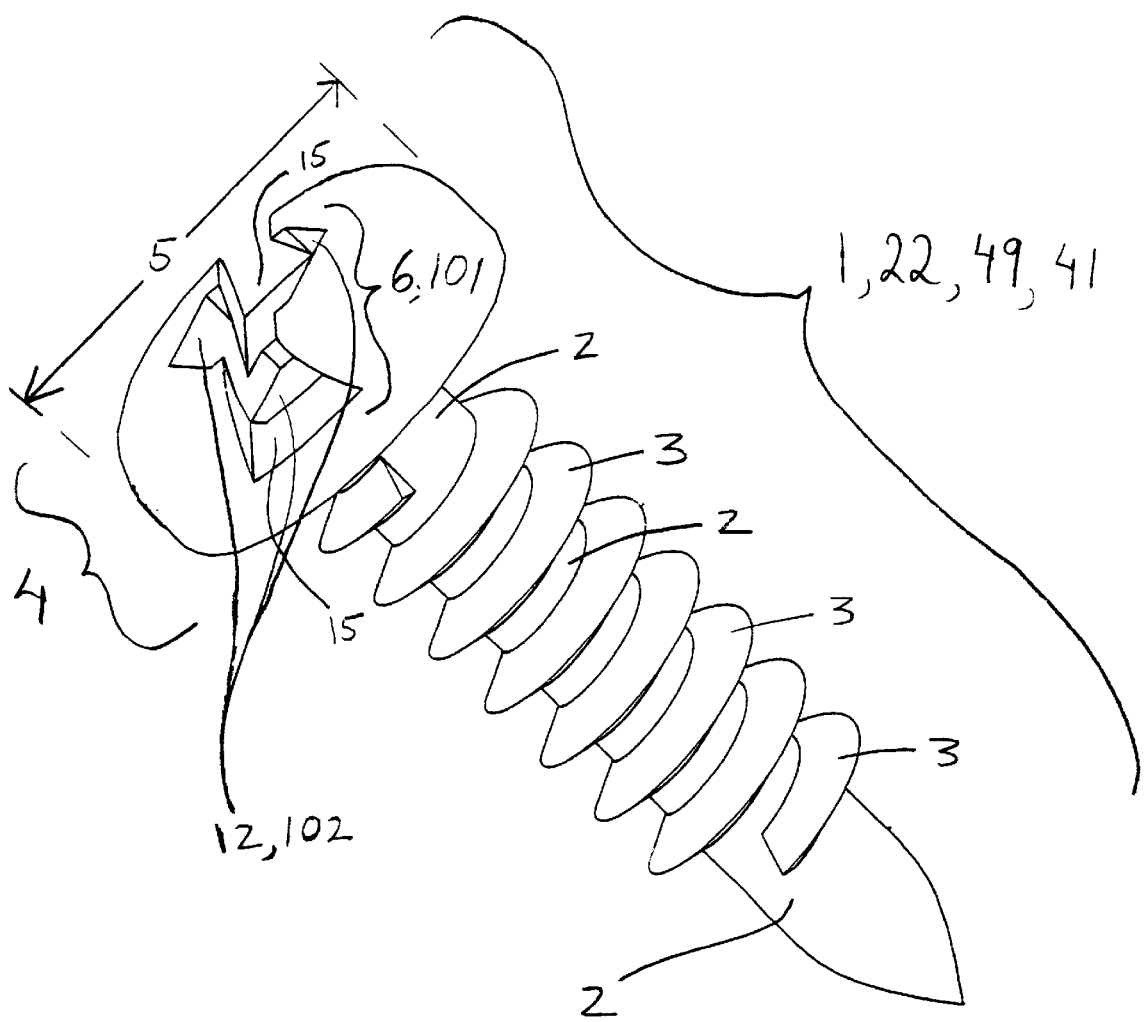
FIG. 1a is a view of at least one embodiment of the fastener apparatus.
Figure 1B:
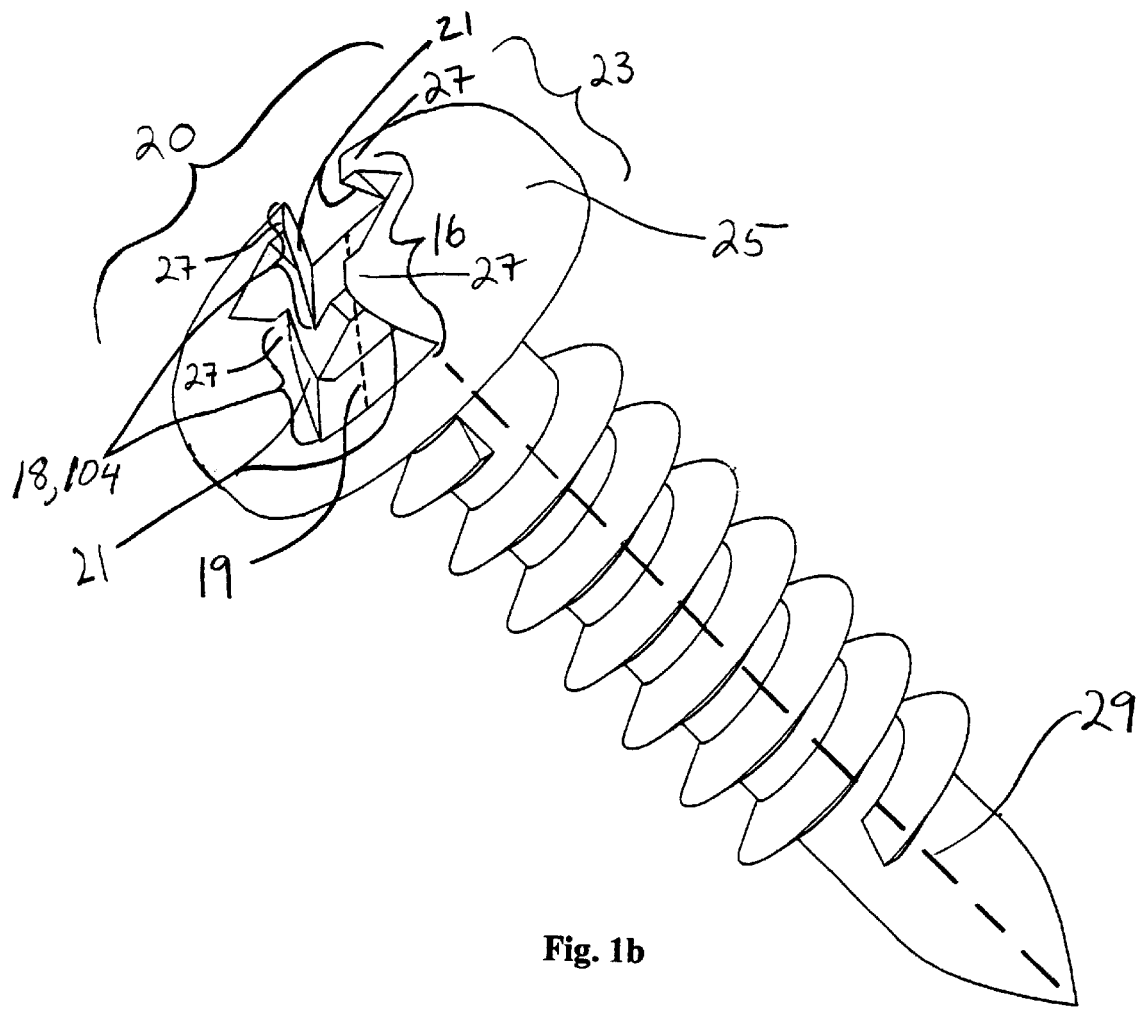
FIG. 1b is a view of at least one embodiment of the fastener apparatus.
Figure 1C:
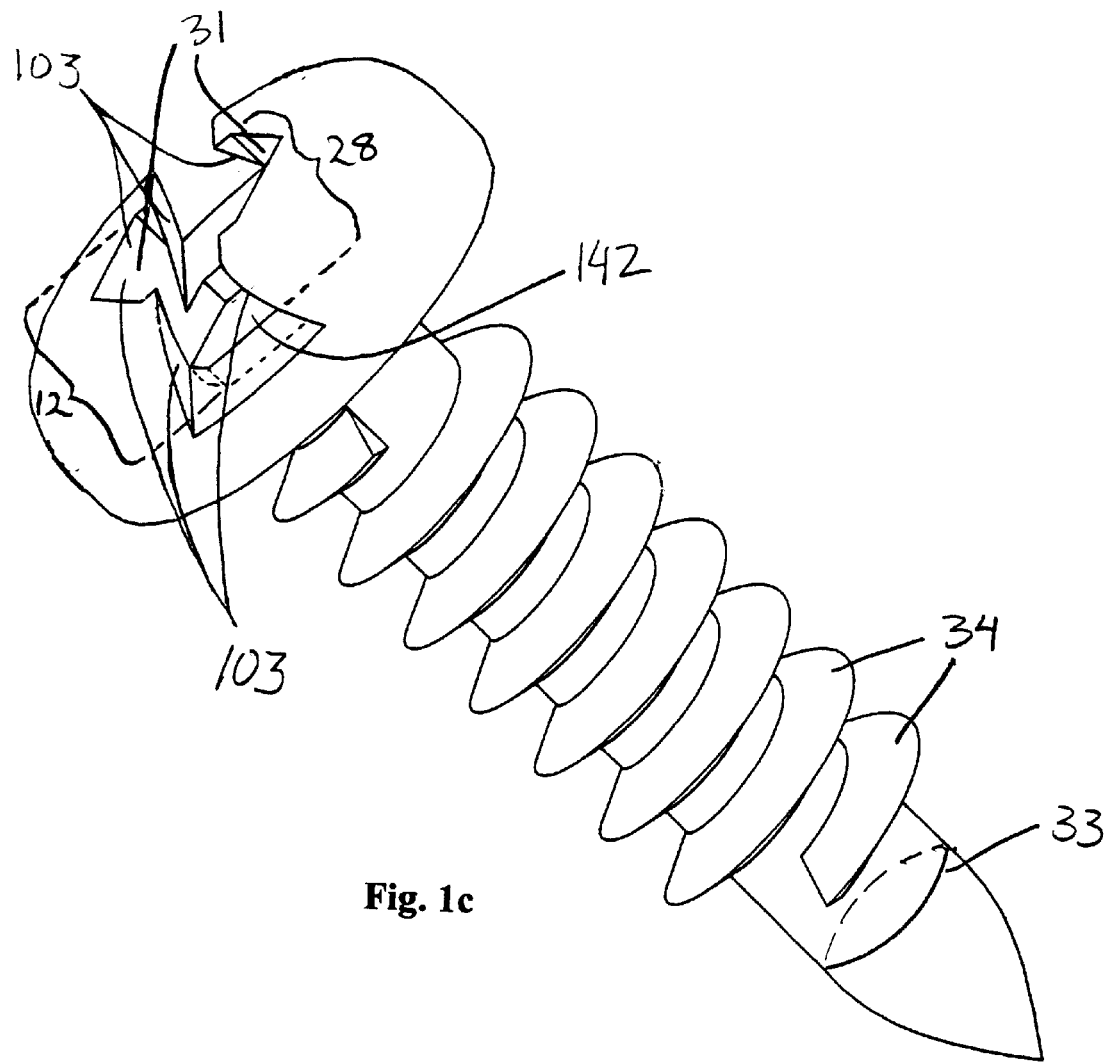
FIG. 1c is a view of at least one embodiment of the fastener apparatus showing different elements.
Figure 2:
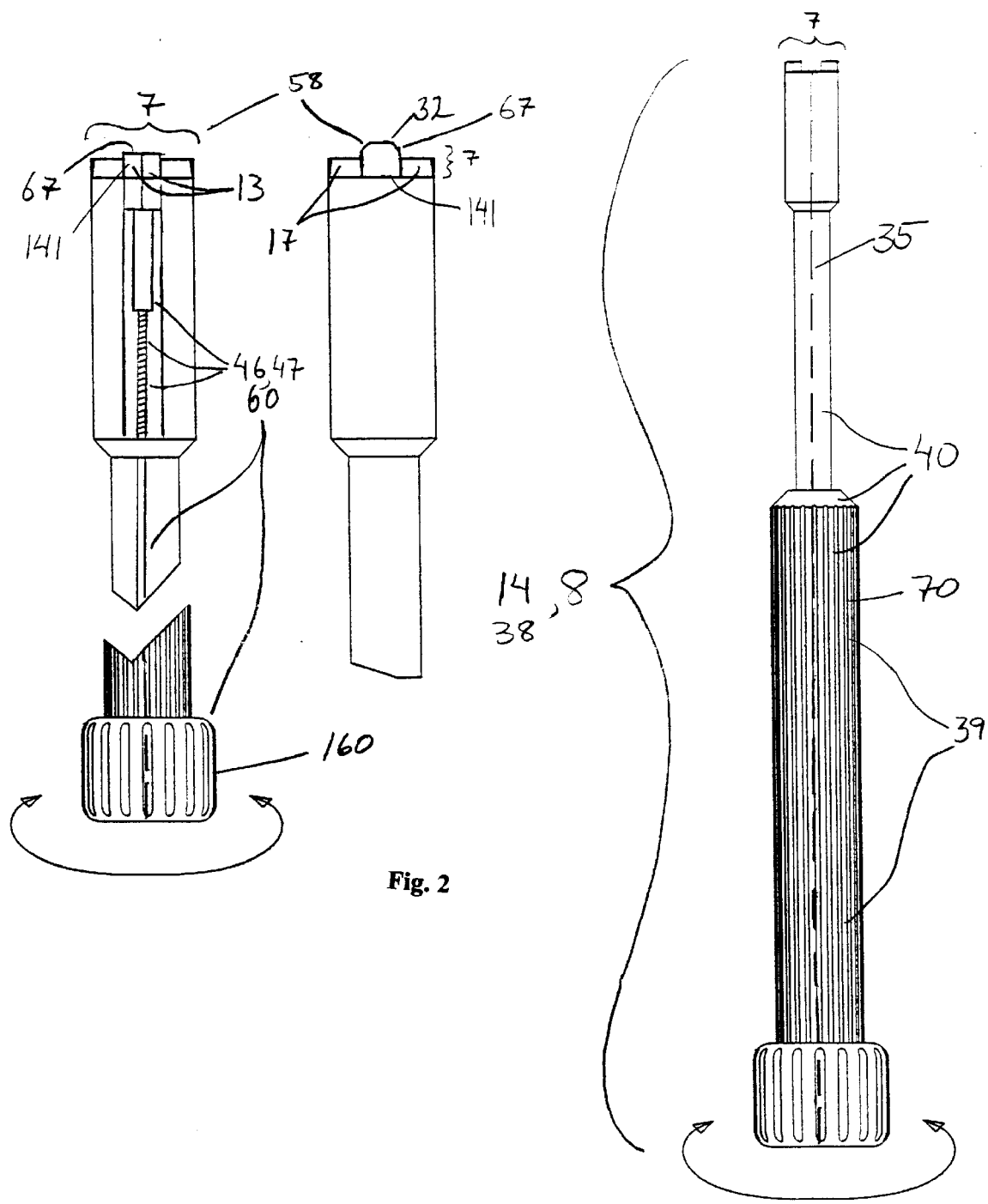
FIG. 2 is a view of at least one embodiment of the fastener driver apparatus, including close up views of different embodiments of the end of the fastener driver apparatus.
Figure 3:
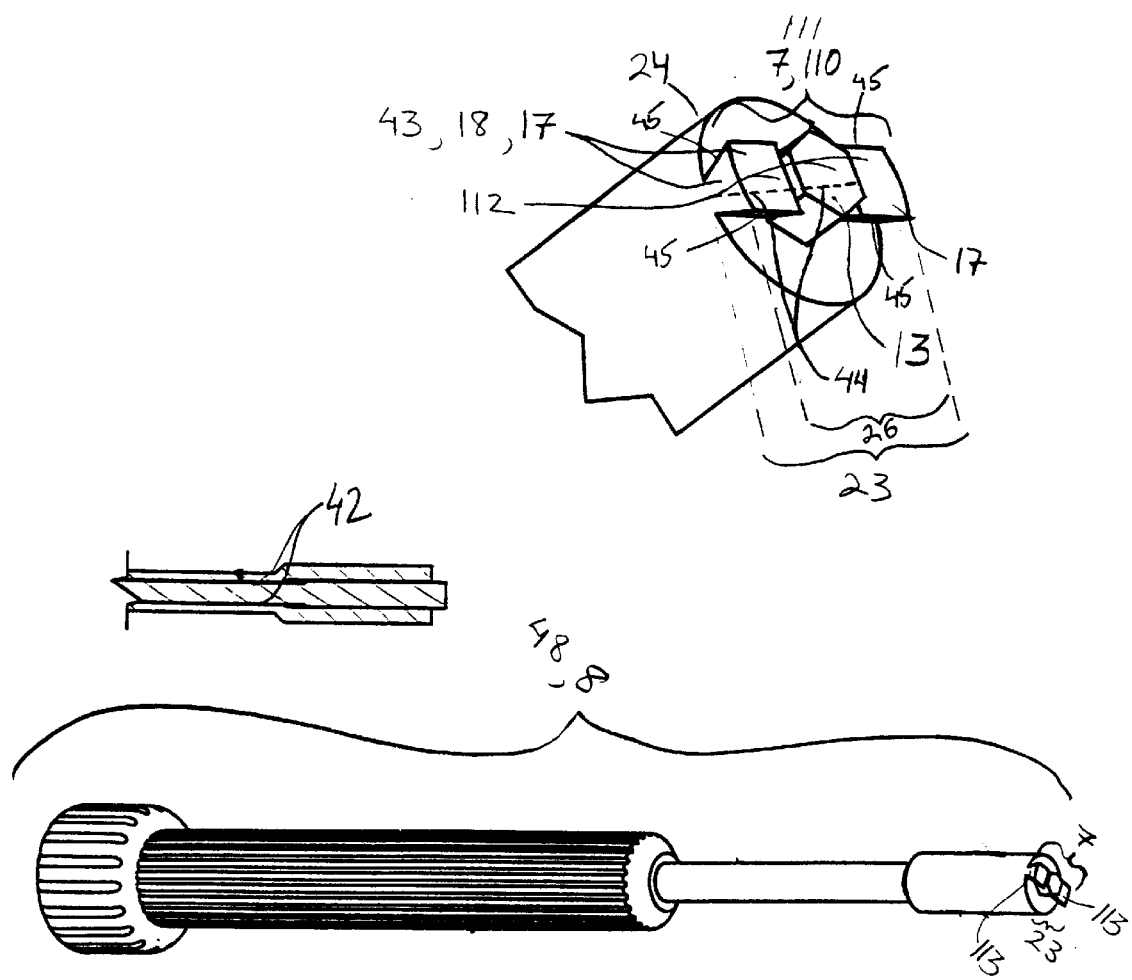
FIG. 3 is another view of at least one embodiment of the fastener driver apparatus, including close up views of different embodiments of the end of the fastener driver apparatus.
Figure 4:
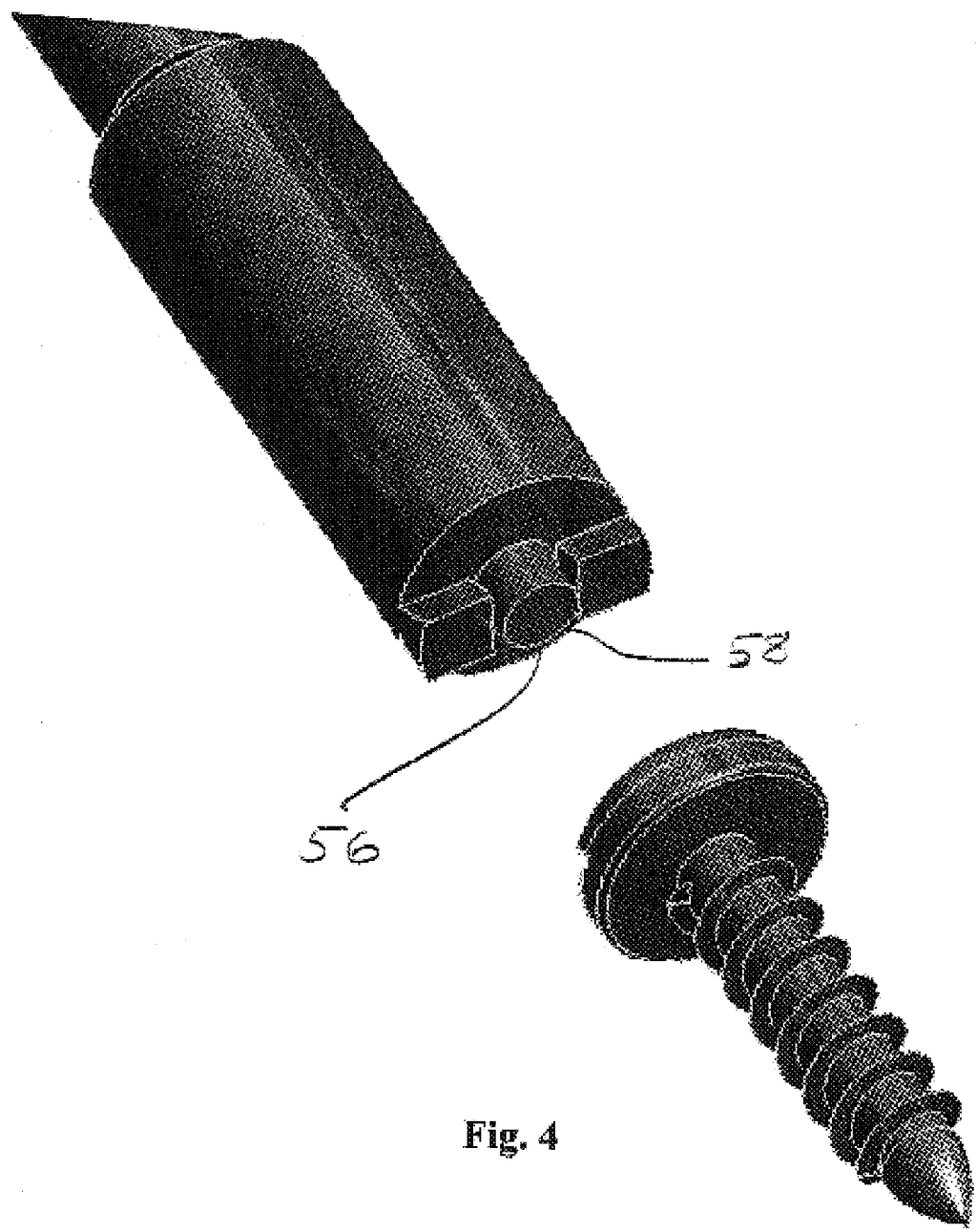
FIG. 4 is a view of at least one embodiment of the fastener and driver system.
Figure 5A:
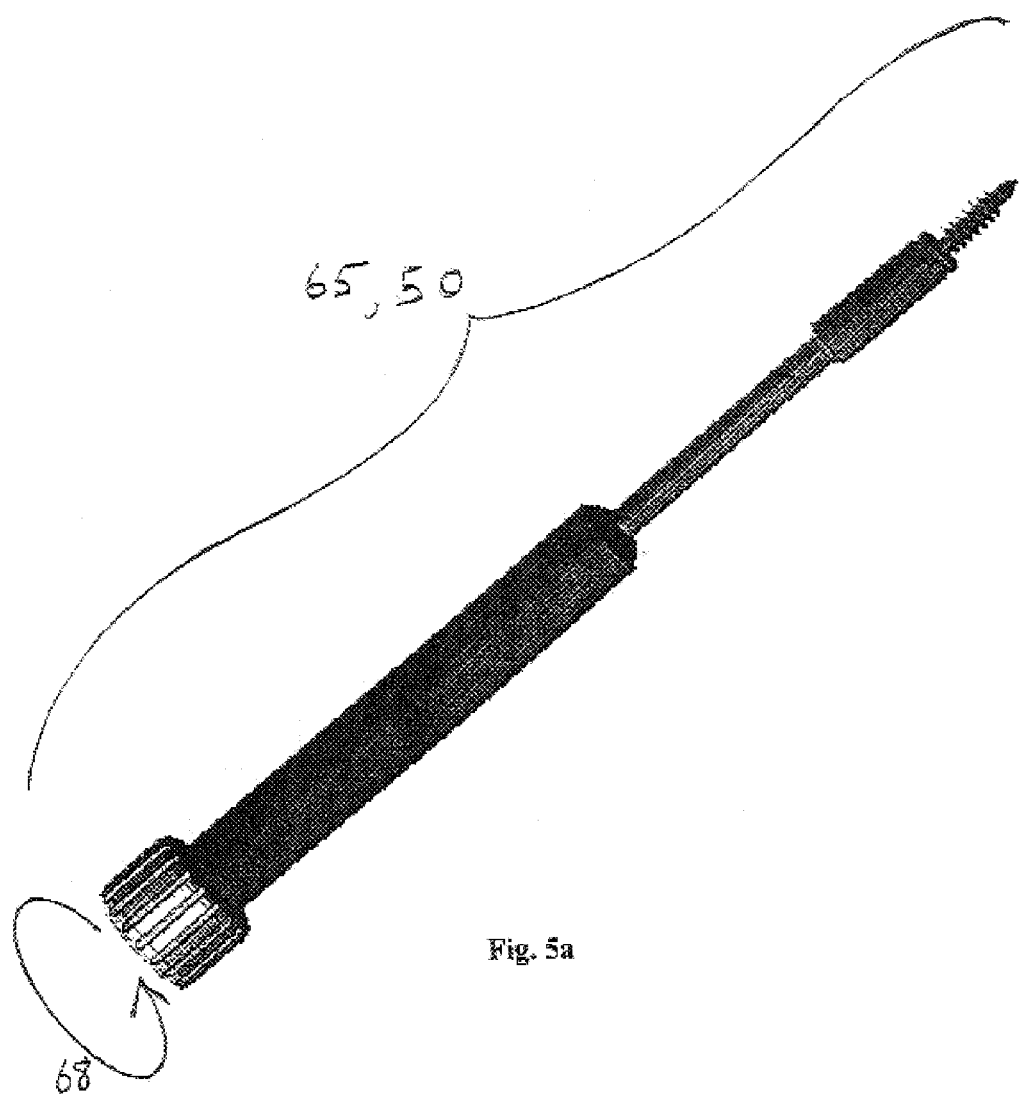
FIG. 5a is a view of at least one embodiment of the fastener and driver system in an engaged configuration.
Figure 5B:
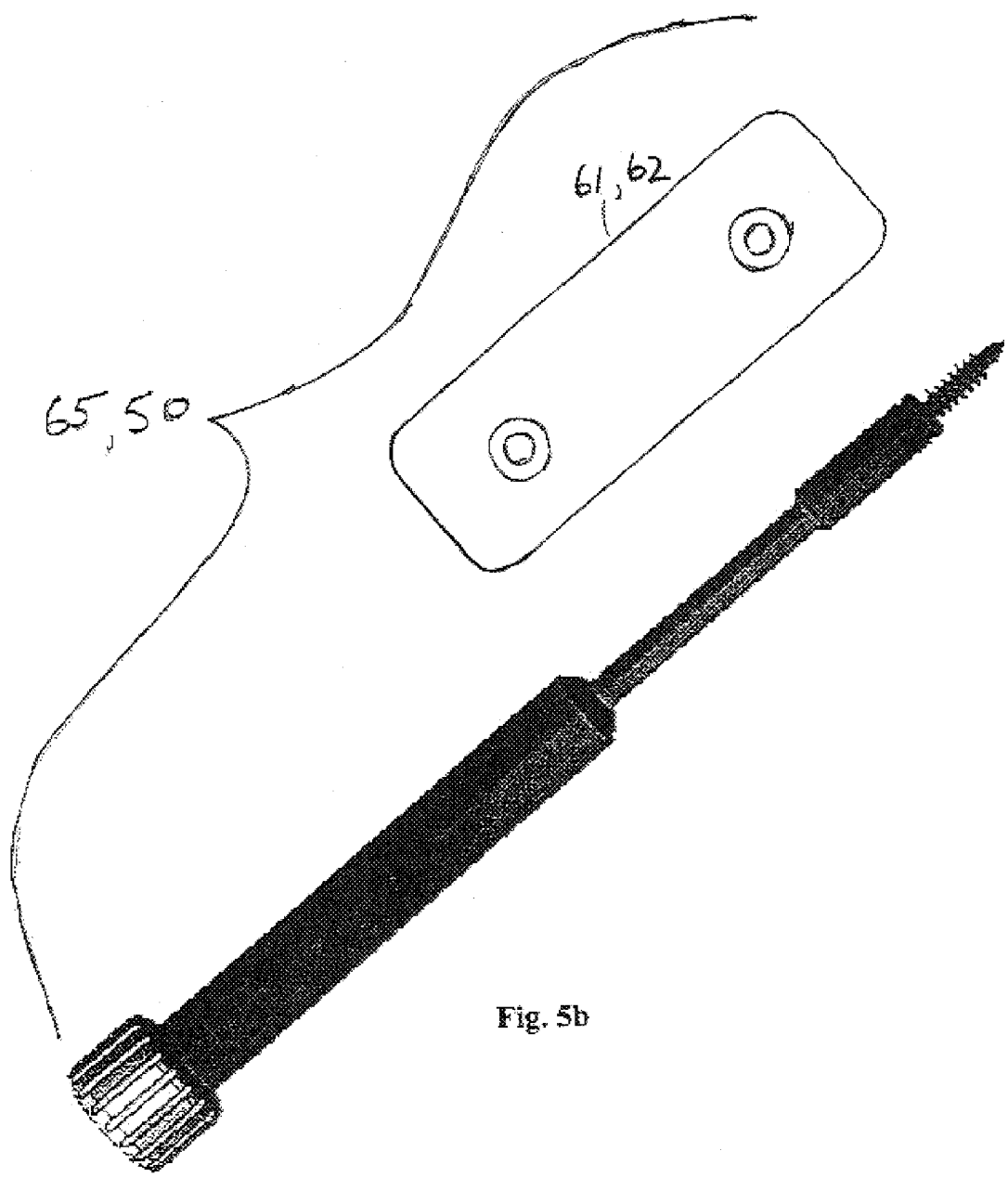
FIG. 5b is a view of at least one embodiment of the fastener and driver system in an engaged configuration, and including an orthopedic plate.
Figure 5C:
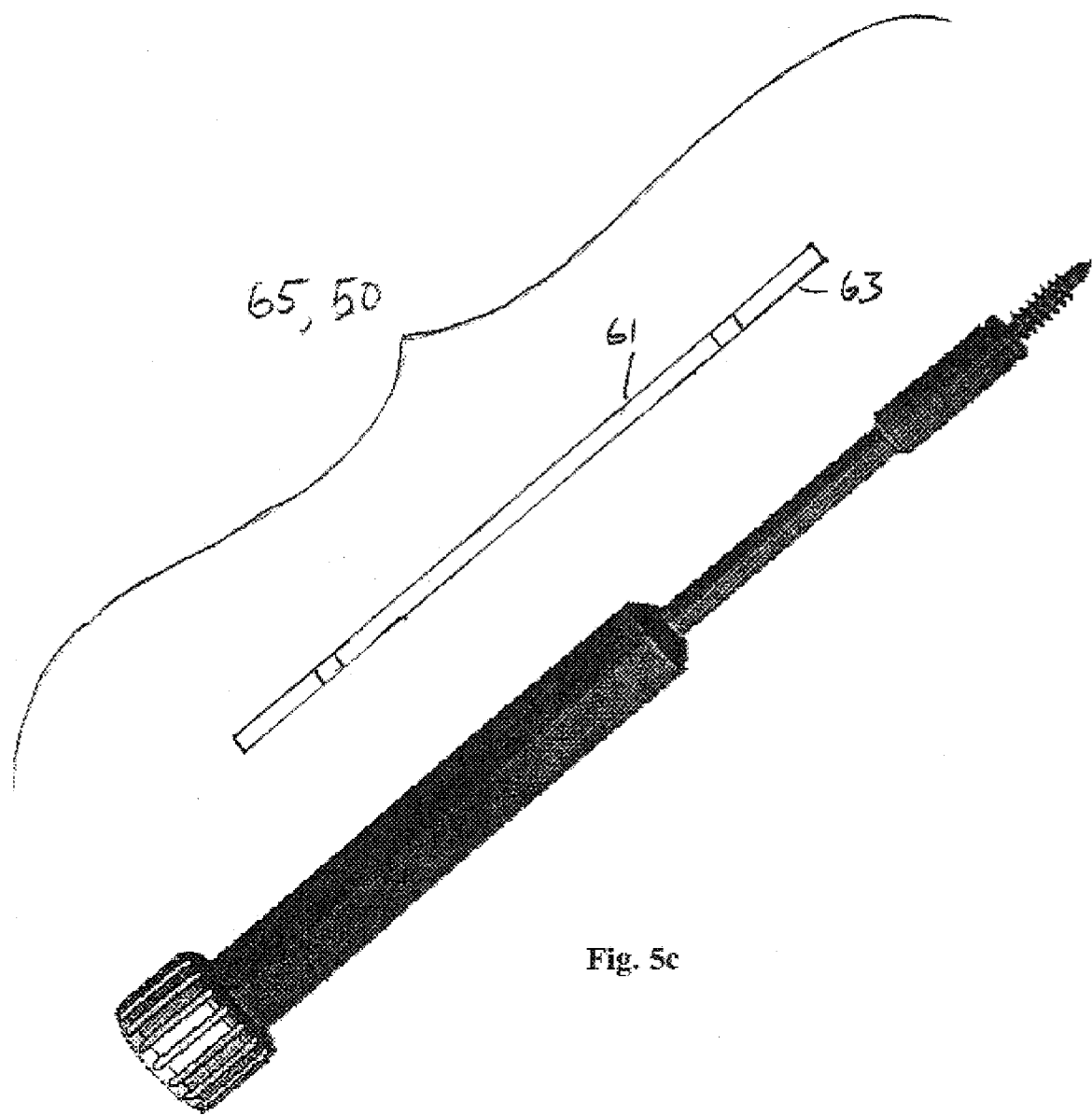
FIG. 5c is a view of at least one embodiment of the fastener and driver system in an engaged configuration, and including an orthopedic rod.
Figure 6:
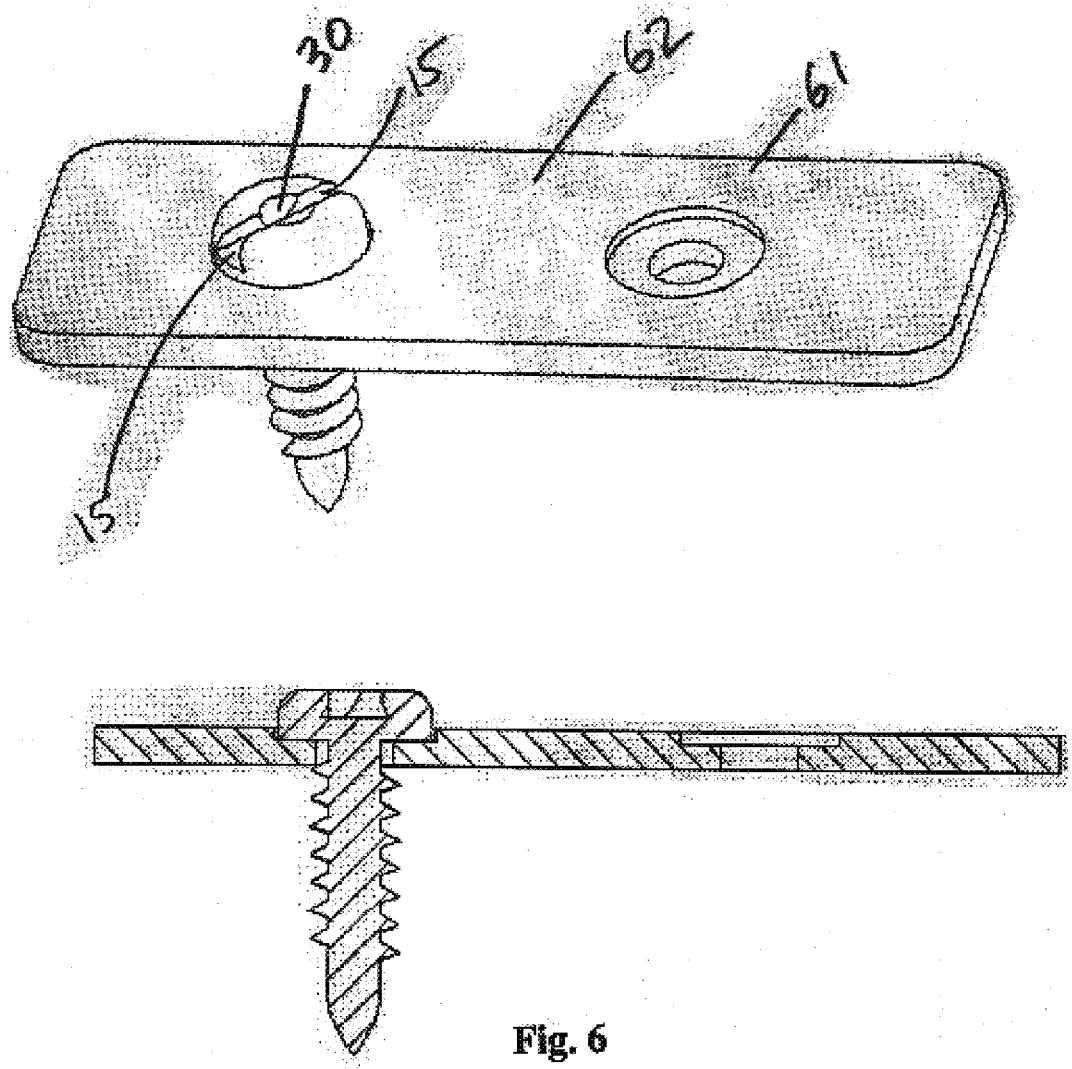
FIG. 6 is a view of at least one embodiment of the fastener as it is used to fasten an orthopedic plate.
Figure 7:
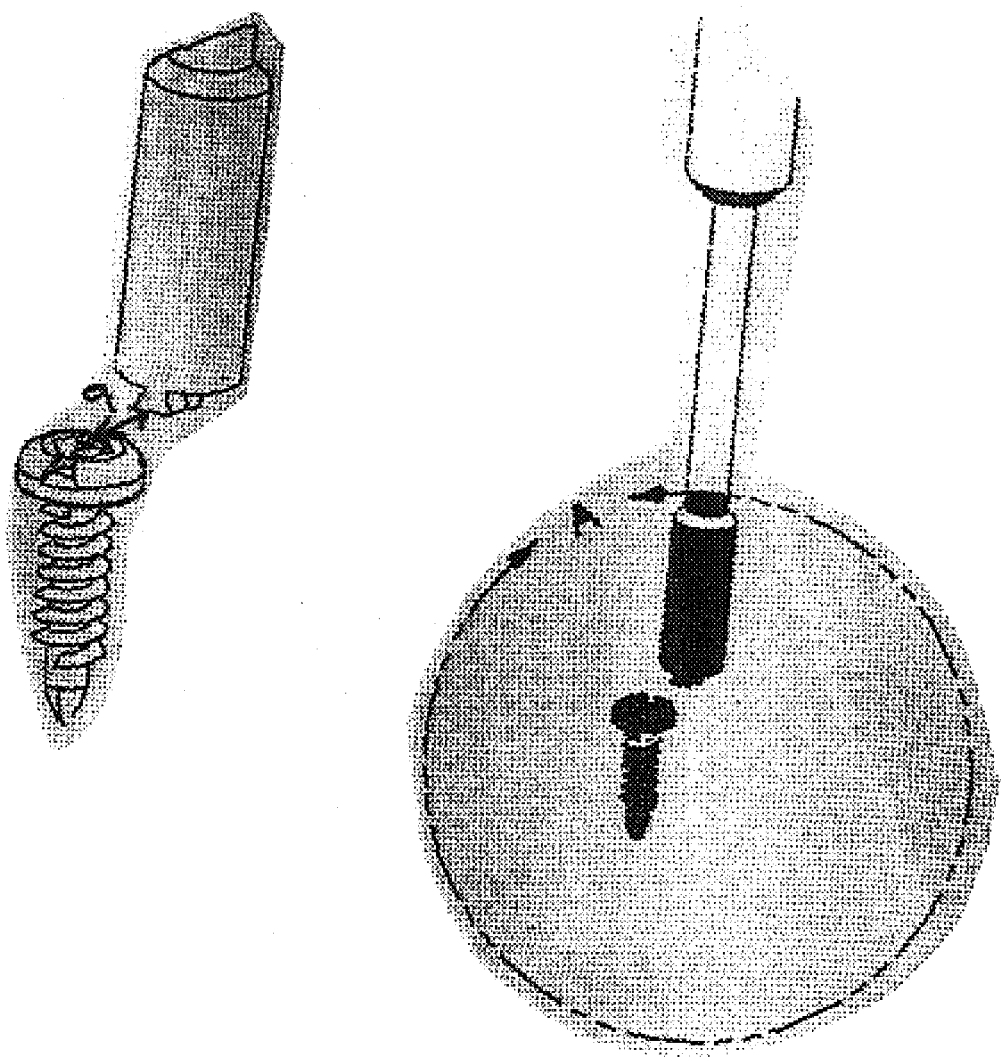
FIG. 7 is a view of at least one embodiment of the fastener and driver system.
Figure 8:
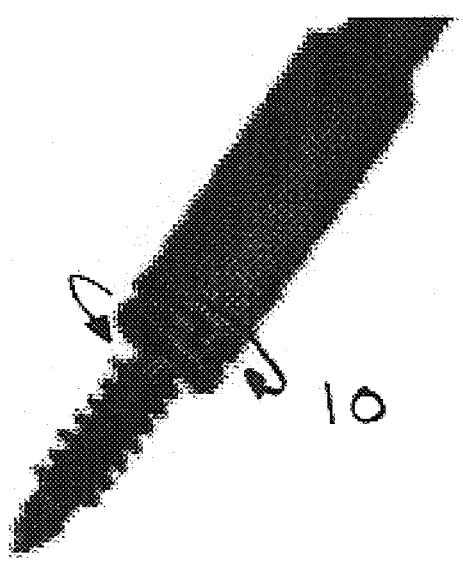
FIG. 8 is a view of at least one embodiment of the fastener and driver system in an engaged configuration.
Figure 9:
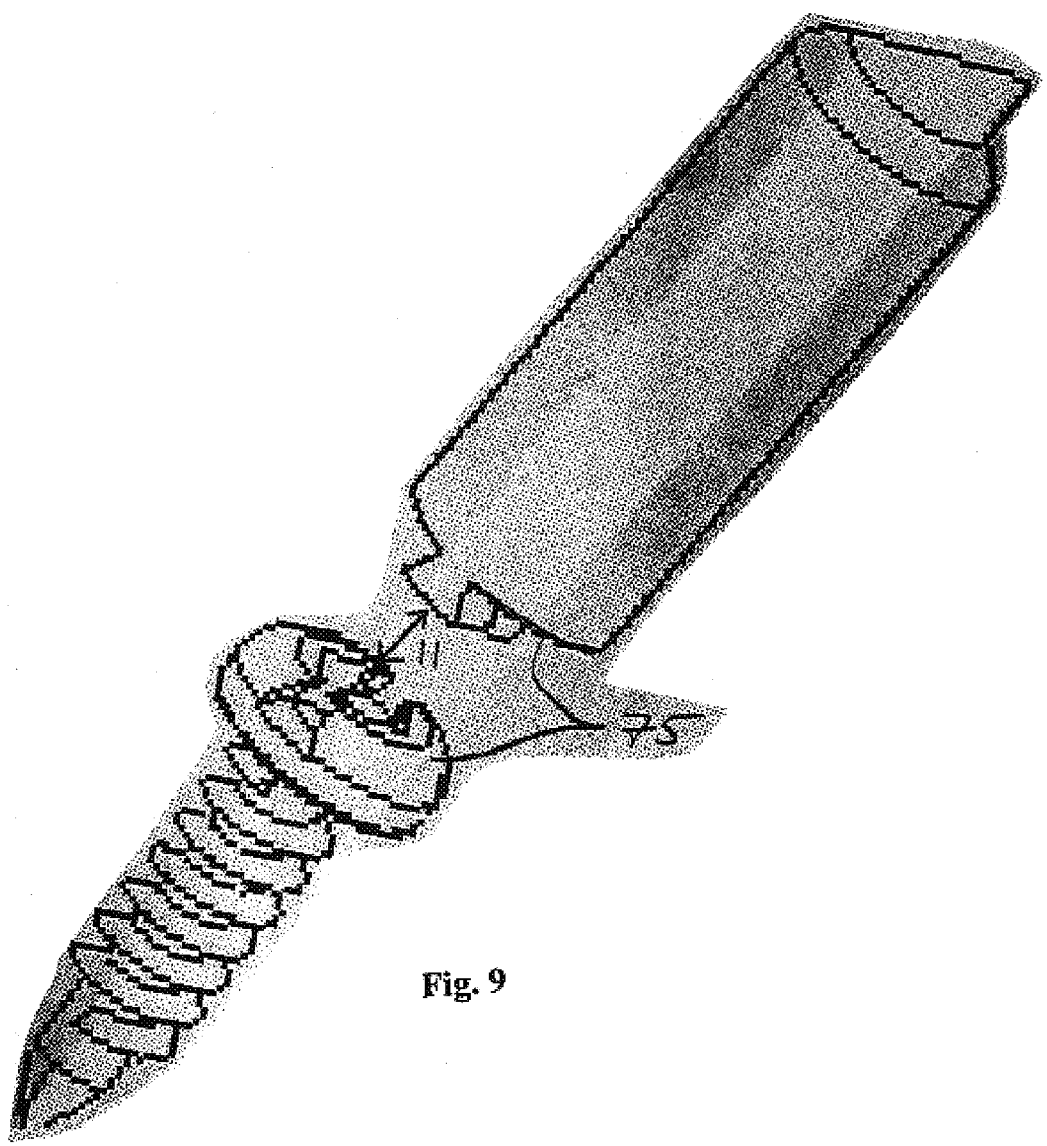
FIG. 9 is a view of at least one embodiment of the fastener and driver system.
Figure 10:
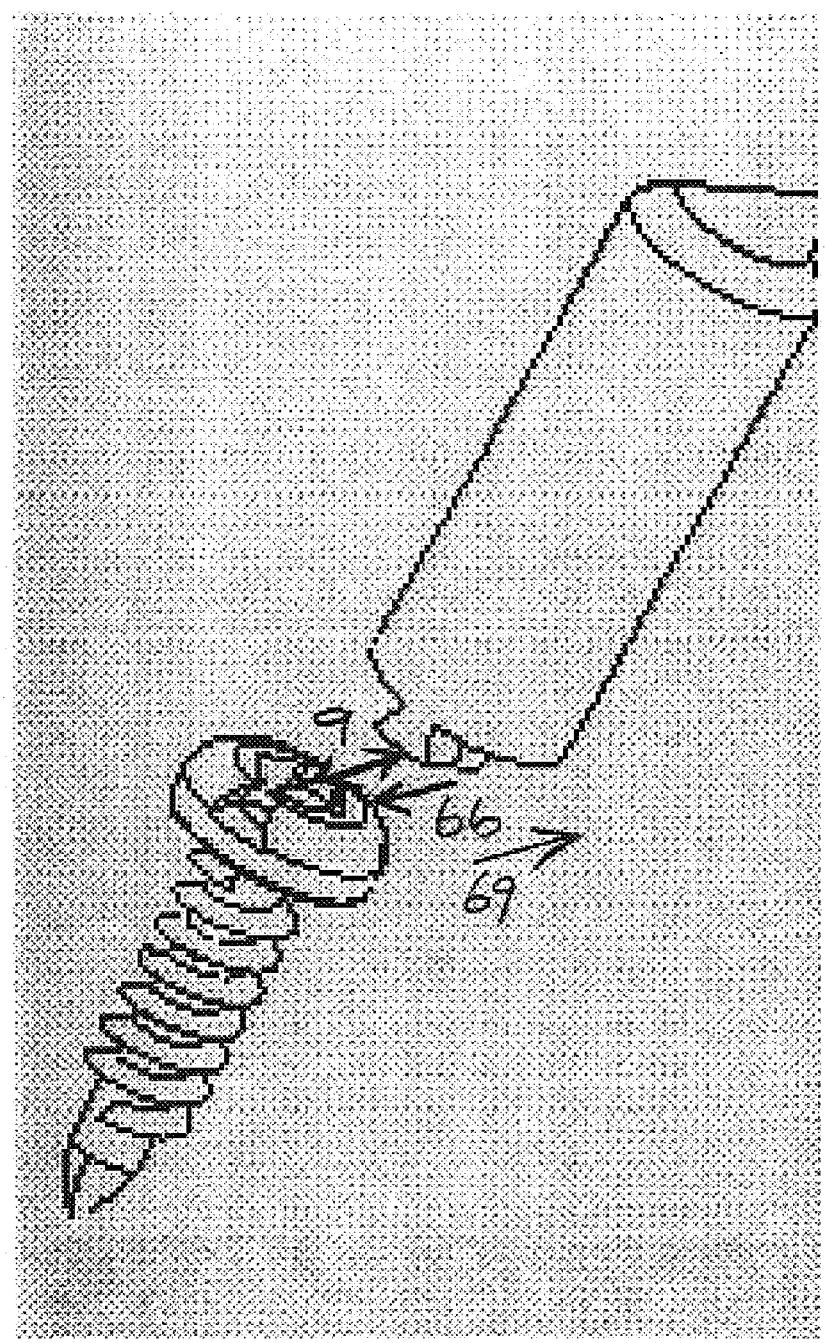
FIG. 10 is a view of at least one embodiment of the fastener and driver system.
Figure 11:
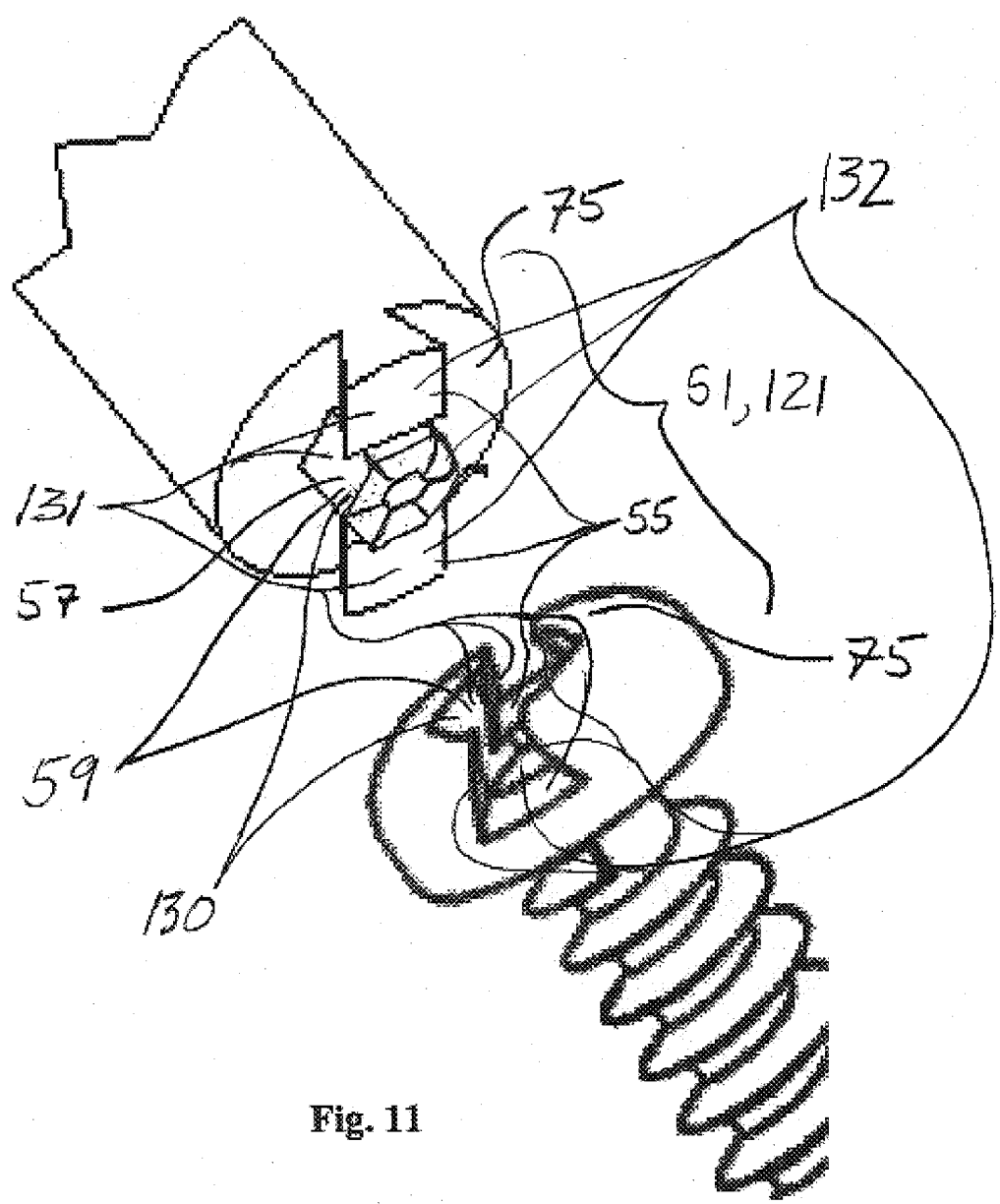
FIG. 11 is a view of at least one embodiment of the fastener and driver system.
Figure 12:
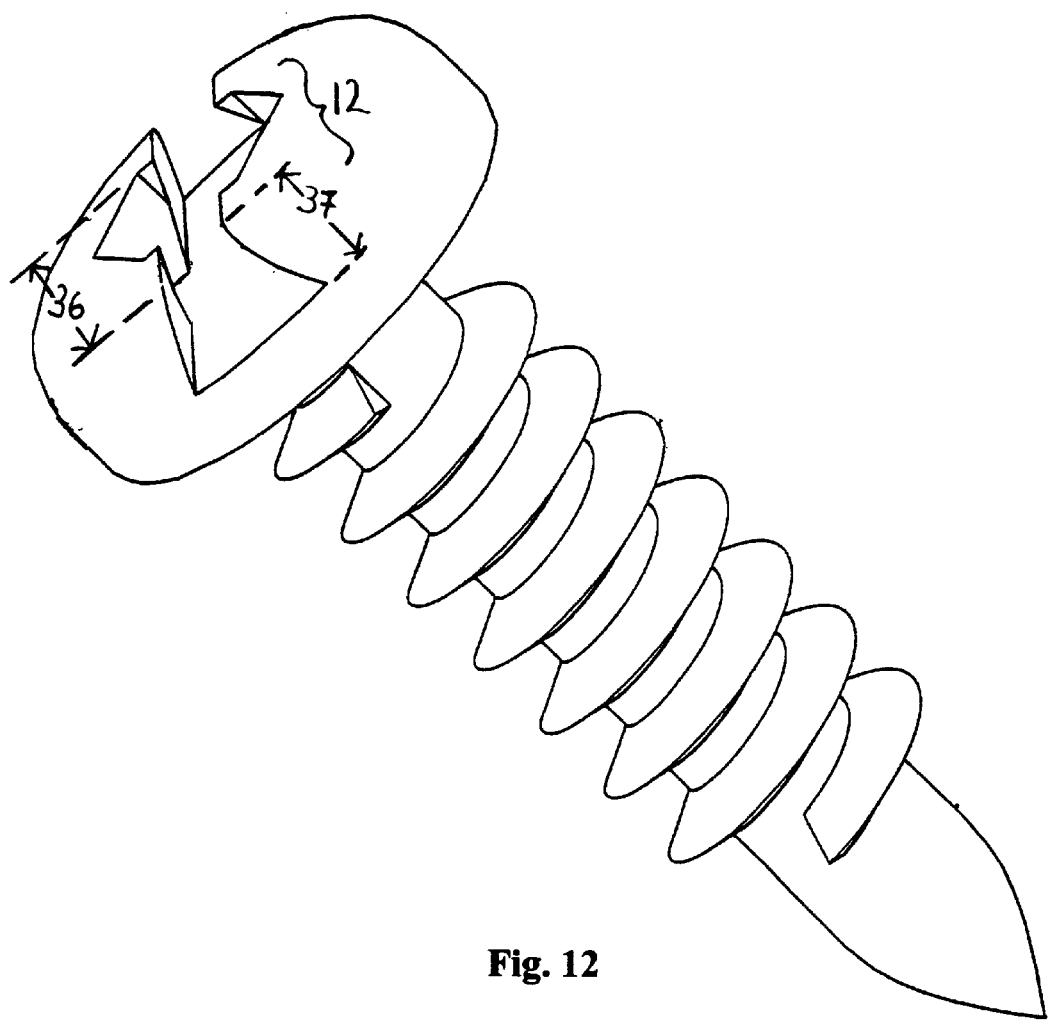
FIG. 12 is a view of at least one embodiment of the fastener apparatus.

At least one embodiment of a bone media fastener apparatus 1 may comprise a shaft element 2, a threaded bone engagement element 3 responsive to the shaft element 2, and a head element 4 responsive to the shaft element 2. The head element 4 may have a larger width dimension 5 than does the threaded bone engagement element 3 and the shaft element 2, and may comprise a fastener-side, positive, complete tri-modal retention element 6 that is engageable with a driver-side, positive, complete tri-modal retention element 7 of a bone media fastener driver element 8. This fastener-side, positive, complete tri-modal retention element may prevent bi-lateral divergence 9, bi-rotational divergence 10, and bi-axial divergence 11. Note that in at least one embodiment, each of these terms refer to driver-from-fastener divergence. The terms "bone", "bone media", and "bone medium" may refer to bone, bone fragments, osseous tissue, fibrous connective tissue, and/or calcified tissue. As long as at least one of the two or more parts that are to be fastened is bone or bone media (as but two examples, one part may be an orthopedic plate 62 or rod 63), then the term bone or bone media is properly applicable. Bi-lateral divergence 9 may refer to positional divergence or motion of the driver away from the fastener in a lateral direction. Note that bi-lateral divergence prevention may not only refer to prevention of divergence in either of the two directions along any slot-like receptors 15 that either the fastener 22 or the driver 14 may comprise, but may also include prevention of lateral divergence in other directions. Bi-rotational divergence 10 may refer to angular displacement of the driver relative to the fastener in either a clockwise or counterclockwise direction. Bi-axial divergence 11 may refer to positional divergence or motion of the driver 14 away from or towards the fastener 22 in an axial direction, where axial direction may refer to along the length axis 35,29 of the driver 14 and/or fastener 22.

The fastener-side, positive, complete tri-modal retention element 6 may comprise a fastener-side, positive complete tri-modal obstructive retention element 101. The term obstructive retention indicates that the retention of the driver 14 by (or to) the fastener 22 is achieved primarily through obstruction of at least one part by at least one other part, as opposed to through friction between parts. The mere presence of some friction will not render inapplicable the characterization of a retention element as obstructive, as the term obstructive merely indicates that more than half of the retention force is achieved through obstruction instead of friction. Frictional retention is deemed to occur whenever at least one of two substantially parallel contacting surfaces is prevented from moving in a direction parallel to the plane of the contacting surfaces by a force that compresses the contacting surfaces against one another. Note also that, e.g., two contacting spheres can be prevented from moving relative to one another by frictional (or frictive) retention because the contacting surfaces are substantially parallel (notwithstanding the fact that the surfaces of which the contacting surfaces are a part are not planar).

The fastener-side, positive complete tri-modal retention element 6, in addition to the fastener-side positive complete tri-modal obstructive retention element 101, may comprise a fastener-side bi-lateral divergence prevention element 102, a fastener-side, bi-rotational divergence prevention element 103, and a fastener-side, bi-axial divergence prevention element 104. The fastener-side bi-lateral divergence prevention element 102 may be any part or element (including one shaped to create a void, space, slot, recess or receptor) located on the fastener 22 that is usable to prevent bi-lateral divergence 9; the fastener-side, bi-rotational divergence prevention element 103 may be any part or element (including one shaped to create a void, space, slot, recess or receptor) located on the fastener 22 that is usable to prevent bi-rotational divergence 10; and the fastener-side, bi-axial divergence prevention element 104 may be any part or element (including one shaped to create a void, space, slot, recess or receptor) located on the fastener 22 that is usable to prevent bi-axial divergence 11. These elements (as well as any other elements presented in the claims) are not necessarily different and discrete elements (although they may be), but instead two or more elements may be the same structural part, e.g. Of course, certain claims may limit certain elements as discrete elements, or may limit one element as comprising one or more other elements. For example, in at least one embodiment, at least a portion of the fastener-side bi-lateral divergence prevention element 102 may comprise a portion of the fastener-side bi-axial divergence prevention element 104, as may be the case where, e.g., an extendable driver part 67 is extendable into a receptor located on the fastener and the extendable driver part end 141 contacts the fastener receptor bottom 142 in an extended configuration 58.

The fastener-side bi-lateral divergence prevention element 102 may comprise a bi-lateral divergence prevention receptor element 12, which may be engageable with an extendable, bi-lateral divergence prevention element 13 of the driver-side, positive retention element 7 to prevent bi-lateral divergence 9. The term extendable may indicate that the referenced element or part is extendable relative to a device such as the driver 14 that the extendable element 13 is a part of. The fastener-side, bi-rotational divergence prevention element 103, and the fastener-side, bi-axial divergence prevention element 104 may together form a fastener-side, combined bi-rotational and bi-axial divergence prevention element 16. This fastener-side combined element 16 may be engageable with a driver-side, combined bi-rotational and bi-axial divergence prevention element 17 of the driver-side, positive retention element 7 of the bone media fastener driver element 8 to prevent bi-rotational and bi-axial divergence 10, 11.

In at least one embodiment, at least a portion of the fastener-side bi-lateral divergence prevention element 102 may comprise a portion of the fastener-side bi-axial divergence prevention element 104. Further, at least a portion of the bi-lateral divergence prevention receptor element 12 may comprise a portion of the fastener-side bi-axial divergence prevention element 104, as may be the case where, e.g., an extendable driver part 67 is extendable into a receptor located on the fastener and the extendable driver part end 141 contacts the fastener receptor bottom 142 in an extended configuration 58.

Additionally, at least a portion of the fastener-side bi-lateral divergence prevention element 102 may comprise a portion of the fastener-side, combined bi-rotational and bi-axial divergence prevention element 16. Also, the bi-lateral divergence prevention receptor element 12 may comprise a portion of the fastener-side, combined bi-rotational and bi-axial divergence prevention element 16. In any of these designs, the fastener-side bi-lateral divergence prevention element 102 may be adapted and dimensioned to interact with a driver part in order to prevent at least some bi-axial divergence (such as movement of the driver 14 towards the fastener 22 along a driver and/or fastener axis 35, 29). Such a design may allow for a tighter retention fit upon engagement of the driver 14 with the fastener 22, including a design where the driver part that the fastener-side bi-lateral divergence prevention element 102 interacts with is an extendable, bi-lateral divergence prevention element 13 that is responsive to an incrementally adjusting engagement activation element 47.

The fastener-side bi-axial divergence prevention element may comprise an axis-orthogonal appendage receptor element 18 established at least partially along a diameter 19 of the fastener face 20; the axis-orthogonal appendage receptor element 18 may comprise at least two distally divergent, diameter-parallel walls 21. The term axis-orthogonal may indicate that the length axis of the referenced term is orthogonal or perpendicular to the driver length axis 35 or fastener length axis 29, whichever device the referenced term is a part of. The term distally is used to indicate in a direction away from the attachment of the driver 14 to the fastener 22, and although the precise location of attachment between the two may be a general area 23 at the terminus of each 24, 25, the very end 26, 27 of each of the termini 24, 25 is deemed the attachment for the purposes of clarity. Thus, distally divergent walls diverge in the direction away from the very end of the relevant device (in the immediately preceding case, the fastener 22). It is important to note that walls can be diameter-parallel walls even though they extend along only a portion of the diameter. The axis-orthogonal appendage receptor element 18 may be adapted to surround at least a portion 28 of the bi-lateral divergence prevention receptor element 12 and may be symmetric about a fastener length axis 29. As used here, symmetric about a fastener length axis 29 indicates that the referenced part or element may be the same on one side of the axis as it is on the other side.

It is important to understand that an element that acts to prevent divergence in any direction need not be able to prevent divergence under all forces, but only under design forces—those forces that might be expected in a certain application. For example, an axis-orthogonal appendage receptor element 18 may prevent bi-axial divergence 11 during orthopedic surgery under a tension load of two lbs. applied by the driver to the fastener, but may not prevent bi-axial divergence 11 under a tension load of two-hundred lbs. because application of such an extreme force is not to be expected during orthopedic surgery.

In at least one embodiment of the bone fastener apparatus 1, the axis-orthogonal appendage receptor element 18 may be adapted to surround at least a portion of the fastener-side bi-lateral divergence prevention element 102. Further, the bi-lateral divergence prevention receptor element 12 may comprise a circular cross-sectional bi-lateral divergence prevention receptor element 30, or it may comprise a non-circular cross-sectional bi-lateral divergence prevention receptor element 31. As such a non-circular cross-sectional bi-lateral divergence prevention receptor element 31 may be usable to prevent bi-rotational divergence 10 of the driver from the fastener upon engagement with a non-circular driver part, the fastener-side, bi-rotational divergence prevention element 103 may be said to comprise at least a portion of the non-circular cross-sectional bi-lateral divergence prevention receptor element 31. Further, the bi-lateral divergence prevention receptor element 12 may be engageable with a tapered, extendable, bi-lateral divergence prevention element 32 of the driver-side, positive complete tri-modal retention element 7 (regardless of the cross-sectional shape of the extendable, bilateral divergence prevention receptor element 12). The taper may also be termed a chamfer. In at least one embodiment of the bone fastener apparatus 1, the bi-lateral divergence prevention receptor element 12 may also exhibit a depth 36 along the fastener length axis 29 that is approximately the same as the depth 37 of the axis-orthogonal appendage receptor element 18 along the fastener length axis.

It is important to note that in a preferred embodiment, the bone fastener apparatus 1 may be a single component which may be made by a variety of means including machining, casting, molding, or other techniques. It may be, e.g., of a generally cylindrical shape 33 into which may be formed threads 34 of various types appropriate to the specific application. The disclosure should also be understood to provide support also for a more generally applicable fastener apparatus 49 that, as described, is not limited by any bone or orthopedic related terms.

The invention also includes a bone media fastener driver apparatus 38 alone and in combination with the bone media fastener apparatus 1. At least one embodiment of a bone media fastener driver apparatus 38 may comprise an applied force receptor element 39, a force-to-bone fastener transfer element 40 (which may be elongated) that is responsive to the applied force receptor element 39, and a driver-side, positive complete tri-modal retention element 7 responsive to the force-to-bone fastener transfer element and engageable with the fastener-side, positive complete tri-modal retention element 6. The driver-side, positive complete tri-modal retention element 7 may comprise a driver-side, positive complete tri-modal obstructive retention element 110. Either type of driver-side complete tri-modal retention element (7 or 110) may comprise a driver-side bi-lateral divergence prevention element 111, a driver-side bi-rotational divergence prevention element 112, and a driver-side, bi-axial divergence prevention element 113. The driver-side bi-lateral divergence prevention element 111 may be any part or element (including one that is extendable) located on the driver 14 that is usable to prevent bi-lateral divergence 9; the driver-side, bi-rotational divergence prevention element 112 may be any part or element located on the driver 14 that is usable to prevent bi-rotational divergence 10; and the driver-side, bi-axial divergence prevention element 113 may be any part or element located on the driver 14 that is usable to prevent bi-axial divergence 11. The driver-side bi-lateral divergence prevention element 111 may comprise an extendable bi-lateral divergence prevention element 13 that is engageable with a bi-lateral divergence prevention receptor element 12 of the fastener-side, positive complete tri-modal retention element 6 of the bone media fastener element 41 to prevent bi-lateral divergence 9. The driver-side bi-lateral divergence prevention element 111, the driver-side bi-rotational divergence prevention element 112, and the driver-side, bi-axial divergence prevention element 113 may each be discrete elements, although in a preferred embodiment, at least two of the three elements are the same part or parts assembly. For example, the driver-side bi-rotational divergence prevention element 112 and the driver-side, bi-axial divergence prevention element 113 together may form a driver-side, combined bi-rotational and bi-axial divergence prevention element 17 that is engageable with a fastener-side, combined bi-rotational and bi-axial divergence prevention element 16 of the fastener-side, positive complete tri-modal retention element 6 of the bone media fastener element 41 to prevent bi-rotational and bi-axial divergence 10, 11.

In at least one embodiment, at least a portion of the driver-side bi-lateral divergence prevention element 111 may comprise a portion of the driver-side bi-axial divergence prevention element 113, as may be the case where, e.g., an extendable driver part 67 is extendable into a receptor located on the fastener 22 and the extendable driver part end 141 contacts the fastener receptor bottom 142 in an extended configuration 58. Further, at least a portion of the extendable bi-lateral divergence prevention element 13 may comprise a portion of the driver-side bi-axial divergence prevention element 113. Additionally, at least a portion of the driver-side bi-lateral divergence prevention element 111 may comprise a portion of the driver-side, combined bi-rotational and bi-axial divergence prevention element 17. Also, the extendable bi-lateral divergence prevention element 13 may comprise a portion of the driver-side, combined bi-rotational and bi-axial divergence prevention element 17. In any of these designs, the driver-side bi-lateral divergence prevention element 111 may be adapted and dimensioned to interact with a fastener part (including a recess, space, slot, void or receptor) in order to prevent at least some bi-axial divergence (such as movement of the driver 14 towards the fastener 22 along a driver and/or fastener axis 35, 29). Such a design may allow for a tighter retention fit upon engagement of the driver 14 with the fastener 22, including the case where the driver part that the fastener-side bi-lateral divergence prevention element 102 interacts with is an extendable, bi-lateral divergence prevention element 13 that is responsive to an incrementally adjusting engagement activation element 47.

The driver-side bi-axial divergence prevention element 113 or the driver-side, combined bi-rotational and bi-axial divergence prevention element 17 may also comprise an axis-orthogonal appendage element 43 such as, e.g., pawls, established at least partially along a diameter of the driver face 44; the axis-orthogonal appendage element 43 may comprise at least two distally convergent, diameter-parallel walls 45. The axis-orthogonal appendage element 43 may be adapted to surround at least a portion of the extendable, bi-lateral divergence prevention element 13 in an extended configuration and may be symmetric about a driver length axis 35.

In at least one embodiment, the extendable bi-lateral divergence prevention element 13 may comprise a non-circular cross-sectional extendable bi-lateral divergence prevention element 57. In such a design, the driver-side, bi-rotational divergence prevention element 112 may comprise at least a portion of the non-circular cross-sectional extendable bi-lateral divergence prevention element 57. The bi-lateral divergence prevention receptor element 12 may be a corresponding non-circular cross-sectional bi-lateral divergence prevention receptor element 31. In any embodiment (regardless of the cross-sectional shape of the extendable, bi-lateral divergence prevention element 13), the extendable, bi-lateral divergence prevention element 13 may be tapered so as to form a tapered, extendable, bi-lateral divergence prevention element 32. By being tapered, the extendable, bi-lateral divergence prevention element 13 may facilitate the axial alignment of the driver 14 with the fastener 22 by improving, upon extension, the axial alignment provided by the user of the apparatus. Further, the extendable, bi-lateral divergence prevention element 13 may be movable along a driver length axis 35.

The bone media fastener driver apparatus 38 may further comprise an engagement activation element 46 to which the extendable, bi-lateral divergence prevention element 13 is responsive. In at least one embodiment, the engagement activation element 46 may be operable by a user (i.e., user operated) and may comprise an incrementally adjusting engagement activation element 47. It may comprise a threaded system 60 and may be operable by a user via a knob 160 or other rotatable part, as but two examples. The disclosure should also be understood to provide support also for a more generally applicable fastener driver apparatus 48 that, as described, is not limited by any bone or orthopedic related terms.

In at least one embodiment, the applied force receptor element 39 may comprise knurling 70. More generally, it may comprise any appropriate treatment or feature to facilitate a proper and secure hand grip. The force-to-bone fastener transfer element 40 may be an elongated force-to-bone fastener transfer element 140 and may have a cylindrical hole 42 established along at least a portion of its length into which may be inserted and inside of which may move the extendable, bi-lateral divergence prevention element 13.

A bone media fastener and driver system 50 may comprise a bone media fastener element 41, a bone media fastener driver element 8, and a positive complete tri-modal retention element 51. The bone media fastener element 41 may comprise a shaft element 2, a threaded bone engagement element 3 that is responsive to the shaft element 2, and a head element 4 that is responsive to the shaft element 2. The bone media fastener driver element 8 may comprise an applied force receptor element 39, and a force-to-bone fastener transfer element 40 responsive to the applied force receptor element 39. The positive complete tri-modal retention element 51 may comprise a positive complete tri-modal obstructive retention element 121. Either the positive complete tri-modal retention element 51 or the positive complete tri-modal obstructive retention element 121 may prevent bi-lateral divergence 9 with a bi-lateral divergence prevention element 130; bi-rotational divergence 10 with a bi-rotational divergence prevention element 131; and bi-axial divergence 11 with a bi-axial divergence prevention element 132. The bi-lateral divergence prevention element 130 may comprise an extendable, bi-lateral divergence prevention element 13.

At least one embodiment of the positive retention element 51 may comprise a discrete bi-lateral divergence prevention element, a discrete bi-rotational divergence prevention element, and a discrete bi-axial divergence prevention element, as there may be discrete elements to prevent each of the three indicated divergent motions. Instead of three discrete elements, the bi-rotational divergence prevention element 131 and the bi-axial divergence prevention element 132 may together form a combined bi-rotational and bi-axial divergence prevention element 55. Any of the three elements may be combined or overlap to some extent, as may any elements indicated in the application. Further, the fact that a second element performs a function that a first element performs does not render inappropriate a reference to the first element according this function.

In at least one embodiment, at least a portion of the bi-lateral divergence prevention element 130 may comprise a portion of the bi-axial divergence prevention element 132, as may be the case where, e.g., an extendable driver part 67 is extendable into a receptor located on the fastener 22 and the extendable driver part end 141 contacts the fastener receptor bottom 142 in an extended configuration 58. Further, at least a portion of the bi-lateral divergence prevention receptor element 12 may comprise a portion of the bi-axial divergence prevention element 132. Additionally, at least a portion of the bi-lateral divergence prevention element 130 may comprise a portion of the combined bi-rotational and bi-axial divergence prevention element 55. Also, the bi-lateral divergence prevention receptor element 12 may comprise a portion of the combined bi-rotational and bi-axial divergence prevention element 55. In any of these designs, the bi-lateral divergence prevention element 130 may be adapted and dimensioned so that a driver part such as the extendable, bi-lateral divergence prevention element 13 interacts with a fastener part such as the bi-lateral divergence prevention receptor element 12 in order to prevent at least some bi-axial divergence (such as movement of the driver 14 towards the fastener 22 along a driver and/or fastener axis 35, 29). Again, such a design may allow for a tighter retention fit upon engagement of the driver 14 with the fastener 22, including the case where the driver part that interacts with a fastener part is an extendable, bi-lateral divergence prevention element 13 that is responsive to an incrementally adjusting engagement activation element 47.

The bi-lateral divergence prevention element 130 may further comprise a bi-lateral divergence prevention receptor element 12 adapted to receive the extendable, bi-lateral divergence prevention element 13. In a preferred embodiment, the bone media fastener driver element 8 may comprise the extendable bi-lateral divergence prevention element 13 and the bone media fastener element 41 may comprise the bi-lateral divergence prevention receptor element 12.

In at least one embodiment of the bone media fastener and driver system 50, the extendable, bi-lateral divergence prevention element 13 may be a circular cross-sectional, extendable, bi-lateral divergence prevention element 56 and the bi-lateral divergence prevention receptor element 12 may be a corresponding circular cross-sectional, bi-lateral divergence prevention receptor element 30. In a different design, the extendable, bi-lateral divergence prevention element 13 may be a non-circular cross-sectional extendable, bi-lateral divergence prevention element 57 and the bi-lateral divergence prevention receptor element 12 may be a corresponding non-circular cross-sectional lateral divergence prevention receptor element 31. In such a non-circular design, the non-circular shape may aid in preventing bi-rotational divergence 10. Thus, the bi-rotational divergence prevention element 131 may be said to comprise at least a portion of the non-circular cross-sectional extendable bi-lateral divergence prevention element 57. Regardless of the shape of the extendable, bi-lateral divergence prevention element 13, the extendable, bi-lateral divergence prevention element 13 may be a tapered, extendable, bi-lateral divergence prevention element 32 and may be movable along a driver length axis 35.

In embodiments of the bone media fastener and driver system 50 having a combined bi-rotational and bi-axial divergence prevention element 55, this element 55 may comprise an axis-orthogonal appendage element 43 and an axis-orthogonal appendage receptor element 18 engageable with the axis-orthogonal appendage element 43. The axis-orthogonal appendage element 43 and the axis-orthogonal appendage receptor element 18 may each be established at least partially along a diameter of a fastener/driver interface 75. The fastener/driver interface 75 may refer to either the fastener end 27 or the driver end 26 that interfaces the corresponding driver end 26 or fastener end 27, respectively. Further, the axis-orthogonal appendage element 43 may comprise at least two distally convergent, diameter-parallel walls 45, as may the axis-orthogonal appendage receptor element 18. In a preferred embodiment, the bone media fastener driver element 8 may comprise the axis-orthogonal appendage element 43 and the bone media fastener element 41 may comprise the axis-orthogonal appendage receptor element 18. Additionally, in a preferred embodiment, the axis-orthogonal appendage element 43 may be adapted to surround at least a portion of the extendable, bi-lateral divergence prevention element 13 in an extended configuration 58 and the axis-orthogonal appendage receptor element 18 may be adapted to surround at least a portion of the bi-lateral divergence prevention receptor element 12.

In at least one embodiment, the bi-lateral divergence prevention element 130 may comprise a fastener axis-to-driver axis alignment facilitation element 59, particularly where the extendable, bi-lateral divergence prevention element is a tapered, extendable, bi-lateral divergence prevention element 32.

The bone media fastener and driver system 50 may further comprise an orthopedic healing aid 61 adapted to respond to the bone media fastener element 41 in an installed configuration. In a preferred embodiment involving the orthopedic healing aid 61, the healing aid 61 is a plate 62 or rod 63 that is placed substantially between the fastener 22 and the bone(s), including bone piece(s).

The system 50 may include an engagement activation element 46 to which the extendable, bi-lateral divergence prevention element 13 is responsive. In at least one embodiment, this engagement activation element 46 is an incrementally adjusting engagement activation element 47, as would be the case if the engagement activation element 46 comprised, e.g., a threaded system 60 aligned along the length of the bone media fastener driver element 8. The disclosure should also be understood to provide support also for a more generally applicable fastener and driver system 65 that, as described, is not limited by any bone or orthopedic related terms.

Associated methods are also within the scope of the inventive technology, including methods of using a bone media fastener 1 and bone media fastener driver 38 in orthopedic surgical application. At least one embodiment of such a method may comprise the steps of establishing a bone media fastener element 41 relative to a bone medium 64, and engaging the bone media fastener element 41 with a bone media fastener driver element 8 to accomplish complete tri-modal retention. Such step of engaging may comprise the steps of engaging to prevent bi-rotational divergence 10, engaging to prevent bi-axial divergence 11 and engaging to prevent bi-lateral divergence 9. In at least one embodiment, the step of engaging the bone media fastener element 41 with a bone media fastener driver element 8 to accomplish complete tri-modal retention may comprise the step of obstructively engaging the bone media fastener element 41 with a bone media fastener driver element 8. The step of engaging to prevent bi-rotational divergence 10 and the step of engaging to prevent bi-axial divergence 11 may be each be accomplished by performing the same driver-to-fastener relative motion, which motion may comprise a fastener end-to-driver end relative lateral aligning motion 66 such as sliding an axis-orthogonal appendage element 43 into an axis-orthogonal appendage receptor element 18 from the side. In at least one embodiment, the step of engaging the bone media fastener element 41 with a bone media fastener driver element 8 to prevent bi-lateral divergence 9 may be accomplished with a driver-to-fastener relative motion that is different from that motion that is used to accomplish each of the steps of engaging the bone media fastener element 41 with a bone media fastener driver element 8 to prevent bi-rotational divergence 10 and engaging the bone media fastener element 41 with a bone media fastener driver element 8 to prevent bi-axial divergence 11. The step of engaging to prevent bi-lateral divergence 11 may comprise a portion of the step of engaging to prevent bi-axial divergence, as may be the case where, e.g., an extendable driver part 67 is extendable into a receptor located on the fastener and the extendable driver part end 141 contacts the fastener receptor bottom 142 in an extended configuration 58.

The step of engaging the bone media fastener element 41 with a bone media fastener driver element 8 to prevent bi-lateral divergence 9 may comprise extending an extendable driver part 67, which step may comprise activating the extendable driver part 67. The step of activating the extendable driver part 67 may comprise activating the extendable driver part 67 after performing the steps of engaging the bone media fastener element 41 with a bone media fastener driver element 8 to prevent bi-rotational divergence 10 and/or engaging the bone media fastener element 41 with a bone media fastener driver element 8 to prevent bi-axial divergence 11.

At least one embodiment of the method of using a bone media fastener 1 and bone media fastener driver 38 in orthopedic surgical application may further comprise the step of applying a torque force 68 to the bone media fastener element 41 by applying the torque force 68 to the bone media fastener driver element 8 after engaging the bone media fastener element 41 with the bone media fastener driver element 8 to accomplish complete tri-modal retention. At least one embodiment of the method may further comprise the step of establishing an orthopedic healing aid 61 substantially between the bone media fastener element 41 and bone media 64. Further, the method of using a bone media fastener 1 and bone media fastener driver 38 in orthopedic surgery may comprise the step of retracting the extendable driver part 67 and performing a fastener end-to-driver end relative lateral dis-aligning motion 69. The disclosure should also be understood to provide support for more generally applicable methods of using a fastener 22 and fastener driver 14 that is not limited by any bone or orthopedic related terms.

As can be easily understood from the foregoing, the basic concepts of the present invention may be embodied in a variety of ways. It involves both exercise techniques as well as devices to accomplish the appropriate exercise. In this application, the fastening techniques are disclosed as part of the results shown to be achieved by the various devices described and as steps which are inherent to utilization. They are simply the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

The discussion included in this nonprovisional application is intended to serve as a basic description. The reader should be aware that the specific discussion may not explicitly describe all embodiments possible; many alternatives may be implicit. It may not explicitly show how each feature or element can actually be representative of a broader function or of a great variety of alternative or equivalent elements. Again, these are implicitly included in this disclosure. Where the invention is described in device-oriented terminology, each element of the device implicitly performs a function. Apparatus claims may not only be included for the device described, but also method or process claims may be included to address the functions the invention and each element performs. Neither the description nor the terminology is intended to limit the scope of the claims included in this nonprovisional patent application. Specifically, this application is to be understood to include support for non-orthopedic analogs of any claims that are indicated as covering an orthopedic application. For example, it should be understood that new claims that essentially are those existing claims that include elements with the term "bone" or "bone media" without these terms may be added to the case at a later time, and that such new claims also find support in this specification.

It should also be understood that a variety of changes may be made without departing from the essence of the invention. Such changes are also implicitly included in the description. They still fall within the scope of this invention. A broad disclosure encompassing both the explicit embodiment(s) shown, the great variety of implicit alternative embodiments, and the broad methods or processes and the like are encompassed by this disclosure and may be relied upon when drafting the claims for the full patent application. It should be understood that such language changes and broad claiming will be accomplished when the applicant later (filed by the required deadline) seeks a patent filing based on this provisional filing. This nonprovisional patent application seeks examination of as broad a base of claims as deemed within the applicant's right and is designed to yield a patent covering numerous aspects of the invention both independently and as an overall system.

Further, each of the various elements of the invention and claims may also be achieved in a variety of manners. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of a "fastener" should be understood to encompass disclosure of the act of "fastening"—whether explicitly discussed or not—and, conversely, were there effectively disclosure of the act of "fastening" such a disclosure should be understood to encompass disclosure of a "fastener" and even a "means for fastening" Such changes and alternative terms are to be understood to be explicitly included in the description.

Any acts of law, statutes, regulations, or rules mentioned in this application for patent; or patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in the Random House Webster's Unabridged Dictionary, second edition are hereby incorporated by reference. Finally, all references listed in the list of References To Be Incorporated By Reference In Accordance With The Patent Application or other information statement filed with the application are hereby appended and hereby incorporated by reference, however, as to each of the above, to the extent that such information or statements incorporated by reference might be considered inconsistent with the patenting of this/these invention(s) such statements are expressly not to be considered as made by the applicant(s).

Thus, the applicant(s) should be understood to claim at least: i) each of the fastener and fastener driver devices as herein disclosed and described, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, and ix) methods and apparatuses substantially as described hereinbefore and with reference to any of the accompanying examples, x) the various combinations and permutations of each of the elements disclosed, and xi) each potentially dependent claim or concept as a dependency on each and every one of the independent claims or concepts presented. In this regard it should be understood that for practical reasons and so as to avoid adding potentially hundreds of claims, the applicant may eventually present claims with initial dependencies only. Support should be understood to exist to the degree required under new matter laws—including but not limited to European Patent Convention Article 123(2) and United States Patent Law 35 USC 132 or other such laws—to permit the addition of any of the various dependencies or other elements presented under one independent claim or concept as dependencies or elements under any other independent claim or concept. Further, if or when used, the use of the transitional phrase "comprising" is used to maintain the "open-end" claims herein, according to traditional claim interpretation. Thus, unless the context requires otherwise, it should be understood that the term "comprise" or variations such as "comprises" or "comprising" are intended to imply the inclusion of a stated element or step or group of elements or steps but not the exclusion of any other element or step or group of elements or steps. Such terms should be interpreted in their most expansive form so as to afford the applicant the broadest coverage legally permissible.

In drafting any claims at any time in this application, it should also be understood that the applicant has intended to capture as full and broad a scope of coverage as legally available. To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Any claims set forth are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

What is claimed is:

1. A bone media fastener and driver system comprising a bone media fastener element that comprises a shaft element, a threaded bone engagement element responsive to said shaft element, and a head element responsive to said shaft element; a bone media fastener driver element that comprises an applied force receptor element and a force-to-bone fastener transfer element responsive to said applied force receptor element; and a positive, complete trimodal retention element.

wherein said bone media fastener element is configured to allow for an initiation of engagement of said bone media fastener driver element with said bone media fastener element from more than one side of said bone medial fastener element.

2. A bone media fastener and driver system as described in claim 1 wherein said positive, complete trimodal retention element comprises a positive, complete trimodal obstructive retention element.

3. A bone media fastener and driver system as described in claim 1 wherein said positive, complete trimodal retention element comprises a bi-lateral divergence prevention element; a bi-rotational divergence prevention element; and a bi-axial divergence prevention element.

4. A bone media fastener and driver system as described in claim 2 wherein said positive, complete tri-modal obstructive retention element comprises a bi-lateral divergence prevention element; a bi-rotational divergence prevention element; and a bi-axial divergence prevenuon element.

5. A bone media fastener and driver system as described in claim 3 or 4 wherein said bi-lateral divergence prevention element comprises an extendable bi-lateral divergence prevention element.

6. A bone media fastener and driver system as described in claim 5 wherein each said bi-lateral divergence prevention element, said bi-rotational divergence prevention element, and said bi-axial divergence prevention element are discrete elements.

7. A bone media fastener and driver system as described in claim 5 wherein said bi-rotational divergence prevention element and said bi-axial divergence prevention element together form a combined, bi-rotational and bi-axial divergence prevention element.

8. A bone media fastener and driver system as described in claim 5 wherein at least a portion of said extendable, bi-lateral divergence prevention element comprises a portion of said bi-axial divergence prevention element.

9. A bone media fastener and driver system as described in claim 7 wherein at least a portion of said extendable, bi-lateral divergence prevention element comprises a portion of said combined bi-rotational and bi-axial divergence prevention element.

10. A bone media fastener and driver system as described in claim 7 wherein said combined bi-rotational and bi-axial divergence prevention element comprises an axis-orthogonal appendage element and an axis-orthogonal appendage receptor element engageable with said axis-orthogonal appendage element.

11. A bone media fastener and driver system as described in claim 10 wherein said axis-orthogonal appendage element and said axis-orthogonal appendage receptor element is each established at least partially along a diameter of a fastener/driver interface.

12. A bone media fastener and driver system as described in claim 11 wherein said axis-orthogonal appendage element comprises at least two distally convergent, diameter-parallel walls.

13. A bone media fastener and driver system as described in claim 12 wherein said axis-orthogonal appendage receptor element comprises at least two distally divergent, diameter-parallel walls.

14. A bone media fastener and driver system as described in claim 10 wherein said bone media fastener driver element comprises said axis-orthogonal appendage element and said bone media fastener element comprises said axis-orthogonal appendage receptor element.

15. A bone media fastener and driver system as described in claim 10 wherein said axis-orthogonal appendage element is adapted to surround at least a portion of said extendable, bi-lateral divergence prevention element in an extended configuration and said axis-orthogonal appendage receptor element is adapted to surround at least a portion of said bi-lateral divergence prevention receptor element.

16. A bone media fastener and driver system as described in claim 10 furter comprising an orthopedic healing aid adapted to respond to said bone media fastener element in an installed configuration, wherein said orthopedic healing aid is selected from the group of healing aids consisting of: a plate and a rod.

17. A bone media fastener and driver system as described in claim 10 further comprising an engagement activation element to which said extendable, bi-lateral divergence prevention element is responsive.

18. A bone media fastener and driver system as described in claim 17 wherein said engagement activation element comprises an incrementally adjusting engagement activation element.

19. A bone media fastener and driver system as described in claim 5 wherein said bi-lateral divergence prevention element further comprises a bi-lateral divergence prevention receptor element adapted to receive said extendable, bi-lateral divergence prevention element.

20. A bone media fastener and driver system as described in claim 5 wherein said extendable, bi-lateral divergence prevention element is movable along a driver length axis.

21. A bone media fastener and driver system as described in claim 19 wherein said bone media fastener driver element comprises said extendable bi-lateral divergence prevention element and said bone media fastener element comprises said bi-lateral divergence prevention receptor element.

22. A bone media fastener and driver system as described in claim 21 wherein said extendable, bi-lateral divergence prevention element comprises a circular cross-sectional, extendable, bi-lateral divergence prevention element and said bi-lateral divergence prevention receptor element comprises a corresponding circular cross-sectional, bi-lateral divergence prevention receptor element.

23. A bone media fastener and driver system as described in claim 21 wherein said extendable, bi-lateral divergence prevention element comprises a tapered, extendable, bi-lateral divergence prevention element.

24. A bone media fastener and driver system as described in claim 19 wherein said extendable, bi-lateral divergence prevention element comprises a non-circular cross-sectional extendable, bi-lateral divergence prevention element and said bi-lateral divergence prevention receptor element comprises a corresponding non-circular cross-sectional lateral divergence prevention receptor element.

25. A bone media fastener and driver system as described in claim 24 wherein said bi-rotational divergence prevention element comprises at least a portion of said non-circular cross-sectional extendable bi-lateral divergence prevention element.

26. A bone media fastener and driver system as described in claim 23 wherein said bi-lateral divergence prevention element further comprises a fastener axis-to-driver axis alignment facilitation element.

27. A bone media fastener and driver system as described in claim 4 wherein said bi-rotational divergence prevention element and said bi-axial divergence prevention element together form a combined, bi-rotational and bi-axial divergence prevention element.

28. A bone media fastener and driver system as described in claim 27 wherein at least a portion of said bi-lateral divergence prevention element comprises a portion of said combined bi-rotational and bi-axial divergence prevention element.

29. A bone media fastener and driver system as described in claim 4 wherein at least a portion of said bi-lateral divergence prevention element comprises a portion of said bi-axial divergence prevention element.

30. A bone media fastener and driver system as described in claim 4 wherein said bi-lateral divergence prevention element comprises a fastener axis-to-driver axis alignment facilitation element.

31. A bone media fastener and driver system as described in claim 4 further comprising an orthopedic healing aid adapted to respond to said bone media fastener element in an installed configuration, wherein said orthopedic healing aid is selected from the group of healing aids consisting of: a plate and a rod.

32. A bone media fastener and driver system as described in claim 4 further comprising an engagement activation element to which said extendable, bi-lateral divergence prevention element is responsive.

33. A bone media fastener and driver system as described in claim 32 wherein said engagement activation element comprises an incrementally adjusting engagement activation element.

34. A bone media fastener apparatus comprising a shaft element, a threaded bone engagement element responsive to said shaft element, and a head element responsive to said shaft element, wherein said head element comprises a fastener-side, positive, complete tri-modal retention element that is engageable with a driver-side, positive, complete tri-modal retention element of a bone media fastener driver element from more than one side of said head element.

35. A bone media fastener apparatus as described in claim 34 wherein said fastener-side, positive complete tri-modal retention element comprises a fastener-side, positive complete tri-modal obstructive retention element.

36. A bone media fastener apparatus as described in claim 34 wherein said fastener-side, positive complete tri-modal retention element comprises a fastener-side bi-lateral divergence prevention element, a fastener-side, bi-rotational divergence prevention element, and a fastener-side, bi-axial divergence prevention element.

37. A bone media fastener apparatus as described in claim 35 wherein said fastener-side, positive complete tri-modal obstructive retention element comprises a fastener-side bi-lateral divergence prevention element, a fastener-side, bi-rotational divergence prevention element, and a fastener-side, bi-axial divergence prevention element.

38. A bone media fastener apparatus as described in claim 36 or 37 wherein said fastener-side bi-lateral divergence prevention element comprises a bi-lateral divergence prevention receptor element.

39. A bone media fastener apparatus as described in claim 37 wherein each said fastener-side bi-lateral divergence prevention element, said fastener-side, bi-rotational divergence prevention element, and said fastener-side, bi-axial divergence prevention element are discrete elements.

40. A bone media fastener apparatus as described in claim 37 wherein said fastener-side, bi-rotational divergence prevention element, and said fastener-side, bi-axial divergence prevention element together form a fastener-side, combined bi-rotational and bi-axial divergence prevention element.

41. A bone media fastener apparatus as described in claim 38 wherein said fastener-side, bi-rotational divergence prevention element, and said fastener-side, bi-axial divergence prevention element together form a fastener-side, combined bi-rotational and bi-axial divergence prevention element.

42. A bone media fastener apparatus as described in claim 37 wherein at least a portion of said fastener-side bi-lateral divergence prevention element comprises a portion of said fastener-side, bi-axial divergence prevention element.

43. A bone media fastener apparatus as described in claim 38 wherein at least a portion of said bi-lateral divergence prevention receptor element comprises a portion of said fastener-side, bi-axial divergence prevention element.

44. A bone media fastener apparatus as described in claim 40 wherein at least a portion of said fastener-side bi-lateral divergence prevention element comprises a portion of said fastener-side, combined bi-rotational and bi-axial divergence prevention element.

45. A bone media fastener apparatus as described in claim 41 wherein at least a portion of said bilateral divergence prevention receptor element comprises a portion of said fastener-side, combined bi-rotational and bi-axial divergence prevention element.

46. A bone media fastener apparatus as described in claim 37 wherein said fastener-side, bi-axial divergence prevention element comprises an axis-orthogonal appendage receptor element established at least partially along a diameter of the fastener face.

47. A bone media fastener apparatus as described in claim 46 wherein said axis-orthogonal appendage receptor element comprises at least two distally divergent, diameter-parallel walls.

48. A bone media fastener apparatus as described in claim 47 wherein said axis-orthogonal appendage receptor element is adapted to surround at least a portion of said fastener-side bi-lateral divergence prevention element.

49. A bone media fastener apparatus as described in claim 41 wherein said bi-lateral divergence prevention receptor element comprises a circular cross-sectional bi-lateral divergence prevention receptor element.

50. A bone media fastener apparatus as described in claim 41 wherein said bi-lateral divergence prevention receptor element comprises a non-circular cross-sectional bi-lateral divergence prevention receptor element.

51. A bone media fastener apparatus as described in claim 50 wherein said fastener-side, bi-rotational divergence prevention element comprises at least a portion of said non-circular cross-sectional bi-lateral divergence prevention receptor element.

52. A bone media fastener apparatus as described in claim 38 wherein said bi-lateral divergence prevention receptor element is engageable with a tapered, extendable, bi-lateral divergence prevention element of said driver-side, positive, complete tri-modal retention element.

53. A bone media fastener driver apparatus comprising an applied force receptor element; a force-to-bone fastener transfer element responsive to said applied force receptor element; a driver-side, positive, complete tri-modal retention element responsive to said force-to-bone fastener transfer element and engageable with a fastener-side, positive, complete tri-modal retention element of said bone media fastener element from more than one side of said bone media fastener element.

54. A bone media fastener driver apparatus as described in claim 53 wherein said driver-side, positive complete tri-modal retention element comprises a driver-side, positive complete tri-modal obstructive retention element.

55. A bone media fastener driver apparatus as described in claim 53 wherein said driver-side, positive complete tri-modal retention element comprises a driver-side bi-lateral divergence prevention element, a driver-side, bi-rotational divergence prevention element, and a driver-side, bi-axial divergence prevention element.

56. A bone media fastener driver apparatus as described in claim 54 wherein said driver-side, positive complete tri-modal obstructive retention element comprises a driver-side bi-lateral divergence prevention element, a driver-side, bi-rotational divergence prevention element, and a driver-side, bi-axial divergence prevention element.

57. A bone media fastener driver apparatus as described in claim 55 or 56 wherein said driver-side bi-lateral divergence prevention element comprises a extendable bi-lateral divergence prevention element.

58. A bone media fastener driver apparatus as described in claim 57 wherein each said driver-side, bi-lateral divergence prevention element, said driver-side, bi-rotational divergence prevention element, and said driver-side, bi-axial divergence prevention element are discrete elements.

59. A bone media fastener driver apparatus as described in claim 53 wherein said driver-side, bi-rotational divergence prevention element and said driver-side bi-axial divergence prevention element together form a driver-side, combined bi-rotational and bi-axial divergence prevention element.

60. A bone media fastener driver apparatus as described in claim 57 wherein said driver-side, bi-rotational divergence prevention element and said driver-side, bi-axial divergence prevention element together form a driver-side, combined bi-rotational and bi-axial divergence prevention element.

61. A bone media fastener driver apparatus as described in claim 56 wherein at least a portion of said driver-side bi-lateral divergence prevention element comprises a portion of said driver-side bi-axial divergence prevention element.

62. A bone media fastener driver apparatus as described in claim 57 wherein at least a portion of said extendable, bi-lateral divergence prevention element comprises a portion of said driver-side, bi-axial divergence prevention element.

63. A bone media fastener driver apparatus as described in claim 59 wherein at least a portion of said driver-side, bi-lateral divergence prevention element comprises a portion of said driver-side, combined bi-rotational and bi-axial divergence prevention element.

64. A bone media fastener driver apparatus as described in claim 60 wherein at least a portion of said extendable, bi-lateral divergence prevention element comprises a portion of said driver-side, combined bi-rotational and bi-axial divergence prevention element.

65. A bone media fastener driver apparatus as described in claim 56 wherein said driver-side, bi-axial divergence prevention element comprises an axis-orthogonal appendage element established at least partially along a diameter of the driver face.

66. A bone media fastener driver apparatus as described in claim 65 wherein said axis-orthogonal appendage element comprises at least two distally convergent, diameter parallel walls.

67. A bone media fastener driver apparatus as described in claim 65 wherein said axis-orthogonal appendage element is adapted to surround at least a portion of said driver-side bi-lateral divergence prevention element.

68. A bone media fastener driver apparatus as described in claim 60 wherein said extendable, bi-lateral divergence prevention element comprises a circular cross-sectional, extendable, bi-lateral divergence prevention element.

69. A bone media fastener driver apparatus as described in claim 57 wherein said extendable bi-lateral divergence prevention element comprises a non-circular cross-sectional extendable bi-lateral divergence prevention element.

70. A bone media fastener driver apparatus as described in claim 69 wherein said driver-side, bi-rotational divergence prevention element comprises at least a portion of said non-circular cross-sectional extendable bi-lateral divergence prevention element.

71. A bone media fastener driver apparatus as described in claim 57 wherein said extendable bi-lateral divergence prevention element comprises a tapered, extendable, bi-lateral divergence prevention element.

72. A bone media fastener driver apparatus as described in claim 53 further comprising an engagement activation element to which said extendable, bi-lateral divergence prevention element is responsive.

73. A bone media fastener driver apparatus as described in claim 72 wherein said engagement activation element comprises an incrementally adjusting engagement activation element.

* * * * *